US006106833A

United States Patent [19]
Ring et al.

[11] Patent Number: 6,106,833
[45] Date of Patent: Aug. 22, 2000

[54] BISPECIFIC ANTIBODIES, METHODS OF PRODUCTION AND USE THEREOF

[75] Inventors: David Ring, Redwood City; Tian-Xiang Shi, Pinole, both of Calif.

[73] Assignee: Chiron Corporation, Emeryville, Calif.

[21] Appl. No.: 08/968,335

[22] Filed: Nov. 12, 1997

Related U.S. Application Data

[60] Continuation of application No. 08/452,809, May 30, 1995, abandoned, which is a division of application No. 08/323, 566, Oct. 17, 1994, abandoned, which is a continuation of application No. 08/141,375, Oct. 22, 1993, abandoned, which is a continuation of application No. 07/605,399, Oct. 19, 1990, abandoned.

[51] Int. Cl.$^7$ .......................... A61K 39/395; C12N 15/06
[52] U.S. Cl. ..................................... 424/136.1; 424/138.1; 424/144.1; 424/153.1; 424/155.1; 424/173.1; 424/174.1; 435/328; 435/330; 435/334; 435/343.1; 435/344; 435/449; 435/71.1; 530/387.3; 530/387.7; 530/387.22; 530/388.73
[58] Field of Search .............................. 424/136.1, 143.1, 424/138.1, 85.1, 144.1, 153.1, 155.1, 173.1, 174.1; 435/326, 328, 330, 334, 343.1, 344, 449, 71.1; 436/547, 548; 530/388.1, 387.3, 387.7, 388.22, 387.22, 388.73

[56] References Cited

U.S. PATENT DOCUMENTS 4,474,893  10/1984  Reading .
4,676,980   6/1987  Segal et al. .

FOREIGN PATENT DOCUMENTS 174810     3/1986  European Pat. Off. .
WO 87/05943 3/1986  European Pat. Off. .
0214640    3/1987  European Pat. Off. .

OTHER PUBLICATIONS

Ferrini et al., Int. J. Cancer 44, 245–250, Aug. 15, 1989.
Young et al., J. Immunol. 145, 607–615, Jul. 15, 1990.
Van Dijk et al. Int J. Cancer 44:738 1989.
Titus et al. The Journal of Immunology vol. 139 3153–3158 No. 9 1987 Waldmann Science vol. 252 p. 1657 1991 (Harris).
Harris TibTech vol. 11, p. 42 1993.
Bohurs et al., *Int. J. Cancer* 7:78–81 (1992).
Bolhuis et al., "Adoptive Immunotherapy of Ovarian Carcinoma with BS–MAb Targeted Lymphocytes: A Multicenter Study," *Int. J. Cancer*: Supplement 7:78–81 (1992).
Bonardi et al., "Initial Experience in Treating Human Lymphoma with a Combination of Bispecific Antibody and Saporin," *Int. J. Cancer*: Supplement 7:73–71 (1992).
DeLau et al., "Absence of Preferential Homologous H/L Chain Association in Hybrid Hybridomas," *The Journal of Immunology* 146(3):906–914 (1991).
de Palazzo et al., "Antitumor Effects of a Bispecific Antibody Targeting CA 19–9 Antigen and CD16," *Cancer Research* 52:5713–5719 (1992).

Demanet et al., "Bispecific Antibody Therapy of Two Murine B–Cell Lymphomas," *Int. J. Cancer* Supplement 7:67–68 (1992).
Fanger et al., "Bispecific Antibodies and Targeted Cellular Cytotoxicity," *Immunology Today* 12(2):51–54 (1991).
Greenman et al., "Comparative Efficiencies of Bispecfic F(ab'y) and Chimeric Mouse/Human IgG Antibodies in Recruiting Cellular Effectors for Cytotoxicity Via Fcy Receptors," *Cancer Immunol. Immunotherapy* 34:361–369 (1992).
Hamada et al., *PNAS* 83:7785 (1986).
Harris et al., *TibTech* 11:42 (1993).
Hird et al., *Genes and Cancer* Wiley and Sing Ltd. p. 183 (1990).
Houghton et al., *Seminars in Oncology* 13(2):165–179 (1986).
Nitta et al., "Preliminary Trial of Specific Targeting Therapy Against Malignant Glioma," *The Lancet* 35:368–371 (1990).
Karpovsky et al., *J. Exp. Med.* 160:1686 (1984).
Perez et al., *Nature* 316:354 (1985).
Ring et al., "Targeted Lysis of Human Breast Cancer Cells by Human Effector Cells Armed With Bispecific Antibody 2B1 (Anti–c–erB–2/Anti–Fcy Receptor III )," *Breast Epithelial Antigens* Abstract pp 91–104 (1991).
Staerz et al., *Proc. Natl Acad. Science* 83:1453–1457 (1986).
Staerz et al., *Immunology Today* 7:241 (1986).
Staerz et al., *Nature* 314:628 (1985).
Titus et al., *J. Immunol.* 138:4018 (1987).
Titus et al., *Journal of Immunology* 139(9):3153–3158 (1987).
Unkeless, *J. Exp. Med* 150(9):580–596 (1979).
Van Dijk et al., *Int. J. Cancer* 44:738–743 (1989).
Waldmann, *Science* 252:1657 (1991).
Weiner et al., "A Human Tumor Xenograft Model of Therapy with a Bispecific Monoclonal Antibody Targeting c–erB–2 and CD16," *Cancer Research* 53:94–100 (1993).
Weiner, George J., "Bispecific IgG and IL–2 Therapy of a Syngeneic B–Cell Lymphoma in Immunocompetent Mice," *Int. J. Cancer*: Supplement 7:63–66 (1992).

*Primary Examiner*—Julie Burke
*Attorney, Agent, or Firm*—Roberta L. Robins; Lisa E. Alexander; Robert P. Blackburn

[57] ABSTRACT

This invention relates generally to the field of immunology, in particular that of antibodies and antibody productions. More specifically, this invention relates to bispecific antibodies, the hybrid hybridomas which produce them, the parent hybridomas, the production and selection of the hybridomas and hybrid hybridomas, and the purification of the bispecific antibodies. Specific examples relate to bispecific monoclonal antibodies which recognize both the human multi-drug resistance antigen, P-glycoprotein and human Fcγ receptor III (hFcγRIII). These bispecific antibodies are useful in killing cancer cells.

10 Claims, 18 Drawing Sheets

| Samples | Total Number K562/R7 Cells | PMNs-K562/R7 Complex | % of K562/R7 in Complex |
| --- | --- | --- | --- |
| 3G8 Supt | 1861 | 41 | 2% |
| 15D3 Supt | 4257 | 516 | 11% |
| | | | |
| Clone 1 | 4225 | 420 | 9% |
| Clone 2 | 4239 | 400 | 9% |
| Clone 3 | 4197 | 438 | 9% |
| Clone 4 | 4141 | 434 | 9% |
| Clone 5 | 1158 | 469 | 29% |
| Clone 6 | 2882 | 422 | 13% |
| Clone 7 | 4227 | 452 | 10% |
| Clone 8 | 1621 | 53 | 3% |
| Clone 9 | 4256 | 455 | 10% |
| Clone 10 | 4589 | 456 | 9% |
| Clone 11 | 5232 | 481 | 8% |
| Clone 12 | 4564 | 461 | 9% |
| Clone 13 | 4435 | 399 | 8% |
| Clone 14 | 4356 | 376 | 8% |
| Clone 15 (34.5) | 715 | 728 | 50% |
| Clone 16 | 5189 | 463 | 5% |
| Clone 17 | 4251 | 452 | 10% |
| Clone 18 (41.6) | 927 | 1093 | 54% |
| Clone 19 | 1822 | 45 | 2% |
| Clone 20 | 4493 | 473 | 9% |

FIG. 1

BISPECIFIC ANTIBODIES, METHODS OF PRODUCTION AND USE THEREOF

This application is a continuation of U.S. application Ser. No. 08/452,809 filed on May 30, 1995, now abandoned, which is a divisional of U.S. application Ser. No. 08/323,566 filed Oct. 17, 1994, now abandoned, which is a continuation of U.S. application Ser. No. 08/141,375 filed Oct. 22, 1993, now abandoned, which is a continuation of U.S. application Ser. No. 07/605,399 filed Oct. 29, 1990, now abandoned.

FIELD OF THE INVENTION

This invention relates to the field of immunology, in particular that of bispecific antibodies useful in killing cancer cells. The bispecific antibody exemplified recognizes both the human multi-drug resistance antigen, P-glycoprotein, and human Fcγ receptor III.

BACKGROUND OF THE INVENTION

The present invention presents bispecific antibodies, the hybrid hybridomas which produce them, the parent hybridomas, the production and selection of the hybridomas and hybrid hybridomas and the purification of the bispecific antibodies. The specific examples are bispecific monoclonal antibodies which recognize both the human multiple-drug resistance (MDR) antigen, P-glycoprotein, and human Fcγ receptor III (hFcγRIII). Background information as to each of the elements is presented below.

1. Hybridomas and Monoclonal Antibodies (MAB)

Antibodies are normally synthesized by lymphoid cells derived from B lymphocytes of bone marrow. Lymphocytes derived from the same clone produce immunoglobulin of a single amino acid sequence. Lymphocytes cannot be directly cultured over long periods of time to produce substantial amounts of their specific antibody. However, Kohler et al., 1975, *Nature*, 256:495, demonstrated that a process of somatic cell fusion, specifically between a lymphocyte and a myeloma cell, could yield hybrid cells which grow in culture and produce a specific antibody called a "monoclonal antibody" (hereinafter also referred to as "MAB"). The resulting hybrid cell was called a "hybridoma". A monoclonal antibody belongs to a group of antibodies whose population is substantially homogeneous, i.e. the individual molecules of the antibody population are identical except for naturally occurring mutations. Myeloma cells are lymphocyte tumor cells which, depending upon the cell strain, frequently produce an antibody themselves, although "non-producing" strains are known.

2. Multiple Drug Resistance in Cells

Certain cells are capable of developing resistance to drugs. Hamster, mouse and human tumor cell lines displaying multiple-drug resistance (MDR) have been reported. A major problem in the chemotherapy of cancer is the development of cross-resistance of some human tumors to multiple chemotherapeutic drugs. The type of multiple-drug resistance is accompanied by a decrease in drug accumulation and an increase in the expression of a multiple drug resistance protein, which is also known as P-glycoprotein or gp170. (Throughout this patent application, the term "P-glycoprotein" shall denote both P-glycoprotein and gp170). P-glycoprotein is a high molecular weight membrane protein (Mw 170–180 kDa) encoded by the MDR1 gene which is often amplified in MDR cells. The complete nucleotide sequence of the coding region of the human MDR1 gene and the complete corresponding amino acid sequence are disclosed in Patent Cooperation Treaty patent application, publication number WO 87/05943, priority date Mar. 28, and Aug. 1, 1986, "Compositions and methods for clones containing DNA sequences associated with multidrug resistance in human cells," to Roninson, I. B. A method of isolating cDNA specific for P-glycoprotein is described in European Patent Application, Publication No. 174,810, date of publication, Mar. 3, 1986, "Multi-drug resistance in mammalian cell lines and isolation of determinant glycoprotein DNA", to Riordan, J. R.

While the "classical" MDR is based on P-glycoprotein, the "non-classical" MDR is based on other mechanisms, some of them as yet undefined. Throughout this patent application, the collective term "MDR phenotype" shall include both the classical and non-classical MDR phenotypes. "MDR markers" or "MDR antigens" include P-glycoprotein and other antigens expressed solely or differentially on cells expressing the MDR phenotype. Different mutant cell lines exhibit different degrees of drug resistance. Examples of cell lines exhibiting the MDR phenotype have been selected for resistance to a single cytotoxic agent. These cell lines also display a broad, unpredictable cross-resistance to a wide variety of unrelated cytotoxic drugs having different chemical structures and targets of action, many of which are used in cancer treatment. This resistance impedes the efficacy of drugs used in chemotherapy to slow down or decrease the multiplication of cancerous cells.

A monoclonal antibody that is capable of recognizing the K562/ADM adriamycin-resistant strain of a human myelogenous leukemia cell line K562 has been disclosed in European Patent Application, Publication No. 214,640 A3, "Monoclonal antibody in relation to drug-resistant cancers and productions thereof," to Tsuruo, T., published Mar. 18, 1987. This monoclonal antibody is produced by a hybridoma formed as a fusion product between a mouse myeloma cell and a spleen cell from a mouse that has been immunized with the K562/ADM strain.

3. Fc Receptors (FcRs)

Fc receptors are found on many cells which participate in immune responses. Fc receptors (FcRs) are cell surface receptors for the Fc portion of immunoglobulin molecules (Igs). Among the human FcRs that have been identified so far are those which recognize IgG (designated FcγR), IgE (Fc$_\epsilon$R$_1$), IgA (Fc$_\alpha$R), and polymerized IgM/A (Fc$_{\mu, \alpha}$R). The different kinds of FcRs are found in the following cell types: Fc$_\epsilon$R$_I$ (mast cells), Fc$_\epsilon$R$_{II}$ (many leukocytes), Fc$_\alpha$R (neutrophils), and Fc$_{\mu, \alpha}$R (glandular epithelium, hepatocytes), according to Hogg, N., 1988, *Immun. Today*, 9:185–86, "The structure and function of Fc receptors". The widely studied Fc$_\gamma$Rs are central in cellular immune defenses, and are responsible for stimulating the release of mediators of inflammation and hydrolytic enzymes involved in the pathogenesis of autoimmune disease (Unkeless, J. C., 1988, *Ann. Rev. Imm.*, 6:251–87, "Structure and function of human and murine receptors for IgG"). The Fc$_\gamma$Rs provide a crucial link between effector cells and the lymphocytes that secrete Ig, since the macrophage/monocyte, polymorphonuclear leukocyte, and natural killer (NK) cell Fc$_\gamma$Rs confer an element of specific recognition mediated by IgG. Id. Human leukocytes have at least three different receptors for IgG: hFc$_\gamma$RI (found on monocytes/macrophages), hFc$_\gamma$RII (on monocytes, neutrophils, eosinophils, platelets, possible B cells, and the K562 cell line), and hFc$_\gamma$RIII (on NK cells, neutrophils, eosinophils, and macrophages). Id.

4. Hybridoma 3G8

Hybridoma 3G8 is a murine hybridoma which secretes a mouse IgG1 MAB that recognizes human Fc$_\gamma$RIII on human and chimpanzee leukocytes. For example, MAB 3G8 recognizes Fc$_\gamma$RIII on neutrophils, monocytes, macrophages, and NK cells. MAB and hybridoma 3G8 are described in Unkeless, et al., supra, and was initially disclosed in Unkeless, J. C., et al., 1979, *J. Exp. Med.*, 150:580–596.

5. Triomas, Hybrid Hybridomas, and Bispecific Antibodies

A bispecific antibody has binding sites for two different antigens within a single antibody molecule. Antigen binding may be simultaneous or sequential. Triomas and hybrid hybridomas are two examples of cell lines that can secrete bispecific antibodies.

Triomas are generally formed from the fusion of a hybridoma and a lymphocyte. Hybrid hybridomas are generally formed by somatic cell fusion of two hybridomas. The hybridomas and lymphocytes each produce a mono-specific antibody, i.e., an antibody in which all binding sites recognize the same antigen. However, triomas and hybrid hybridomas may synthesize light and heavy chains of both parental types, and a bispecific antibody is composed of both light and heavy chains of both fusing partners. For an IgG producing cell, if the light and heavy chains of both kinds are made in equivalent amounts and combined randomly, at least one-eighth of the antibodies produced will be bispecific antibodies. However, in practice, due to preferential pairing of homologous light and heavy chains, many IgG/IgG fusions produce more than one-eighth bispecific antibody. It is also possible that a hybrid hybridoma or trioma may make little or no bispecific antibody, if heterologous heavy chain/heavy chain pairing is disfavored.

Examples of bispecific antibodies produced by a hybrid hybridoma or a trioma are disclosed in "Recombinant Monoclonal Antibodies", U.S. Pat. No. 4,474,893, to Reading, C. L., issued Oct. 2, 1984. Bispecific antibodies have been constructed which have both an anti-T cell and an anti-tumor antigen activity. Initially, a bispecific antibody conjugate was constructed by chemical means (Staerz et al., 1985, *Nature*, 314:628, and Perez, et al., 1985, *Nature*, 316:354). Later, hybridoma technology was employed (Staerz & Bevan, 1986, *PNAS (USA)*, 83:1453, and Staerz & Bevan, 1986, *Immunology Today*, 7:241). The bispecific antibodies exert their effect by binding to both a tumor cell or other form of target cells, such as a virally infected cell, and to a T-cell thereby causing the destruction of the former by the latter.

Unlike the bispecific antibody prepared by the hybrid hybridomas technology described above, the chemically constructed bispecific antibody are prepared by chemically cross-linking heterologous Fab or F(ab')$_2$ fragments by means of chemicals such as heterobifunctional reagent succinimidyl-3-(2-pyridyldithiol)-propionate (SPDP, Pierce Chemicals, Rockford, Ill.). The Fab and F(ab')$_2$ fragments are obtained from intact antibody by digesting it with papain or pepsin, respectively. (For the procedures for chemically constructing such bispecific antibodies, see e.g., Karpovsky, B. et al., 1984, *J. Exp. Med.*, 160:1686; Titus, J. A. et al., 1987, *J. Immunol.*, 138:4018). A chemically constructed bispecific antibody consisting of MAB 3G8 chemically cross-linked to a melanoma specific MAB could direct Fc$\gamma$RIII bearing lymphocytes to kill melanoma cells both in vitro and in nude mice. Titus, J. A., et al., 1987, *J. Immunol.*, 139:3153. Further, another chemically constructed bispecific antibody anti-CD3/MRK16, was reactive with P-glycoprotein on MDR cells and CD3 antigen on T-lymphocytes. The anti-CD3/MRK16 bispecific antibody was found to induce lysis of MDR tumor cells in vitro. Van Dijk, J. et al., *Int. J. Cancer*, 44: 738 (1989). However, none of the above references discloses a bispecific antibody, produced by the hybrid hybridoma technology, which recognizes tumor cells exhibiting the MDR phenotype and cytotoxic cells with human Fc$\gamma$RIIIs.

SUMMARY OF THE INVENTION

One aspect of the invention presents bispecific antibodies which bind to and are capable of cross-linking tumor cells expressing the MDR phenotype and cytotoxic cells with hFcR receptors, thereby facilitating the lysis of the tumor cells by the cytotoxic cells.

Another aspect of the invention presents bispecific antibodies which are capable of binding to cytotoxic and tumor cells wherein the tumor cells over-express P-glycoprotein; examples of the cytotoxic cells are those expressing hFc$\gamma$RIII.

Another aspect of the invention presents hybrid hybridomas which produce the above bispecific antibodies.

A further aspect of the invention presents composition comprising the above bispecific antibodies in a physiologically acceptable carrier.

A further aspect of the invention presents methods for treating a disease state using the bispecific antibodies, in particular, the disease state is caused by tumor cells which exhibit the MDR phenotype, in particular the over-expression of P-glycoprotein. Further, activating factors, which have the effect of stimulating the cytotoxic activity, growth or production of the effector cells can also be administered as part of the treatment regimen, either separately from, or as part of a composition comprising the bispecific antibodies. The activating factor(s) can also be administered before or during the treatment regimen. Throughout this patent application, it is contemplated that one or more activating factor(s) may be used. Examples of the activating factors are interleukin-2 (IL-2) and macrophage colony-stimulating factor (M-CSF).

A further aspect of the invention presents an armed effector cell composition. More specifically, the composition comprises effector cells, more preferably cytotoxic cells, expressing hFc$\gamma$RIII, dispersed in a physiologically tolerable carrier; the effector cells being armed (bound) with bispecific antibodies which recognize hFc$\gamma$RIII and MDR marker. The preferred MDR marker is P-glycoprotein. The armed effector cells are in an amount effective to kill the target cells. The preferred target cells are tumor cells exhibiting the MDR phenotype, and more preferably the target cells over-express P-glycoprotein when compared to normal cells.

A further aspect of the invention presents methods for treating a disease state using an armed effector cell composition comprising effector cells, more preferably cytotoxic cells, armed with the bispecific antibodies. Before arming the effector or cytotoxic cells with the bispecific antibodies, the cells can be activated with activating factor(s). Alternatively, the activating factor(s) can be administered to the patient before or during treatment, either separately from or as part of the armed effector cell composition.

A further aspect of the invention presents methods for selecting fused cells.

BRIEF DESCRIPTION OF THE DRAWINGS

FIG. 1 presents the result of the bridge assay for the antibodies produced by 20 selected quadromas.

DETAILED DESCRIPTION OF THE INVENTION

Figure 2:
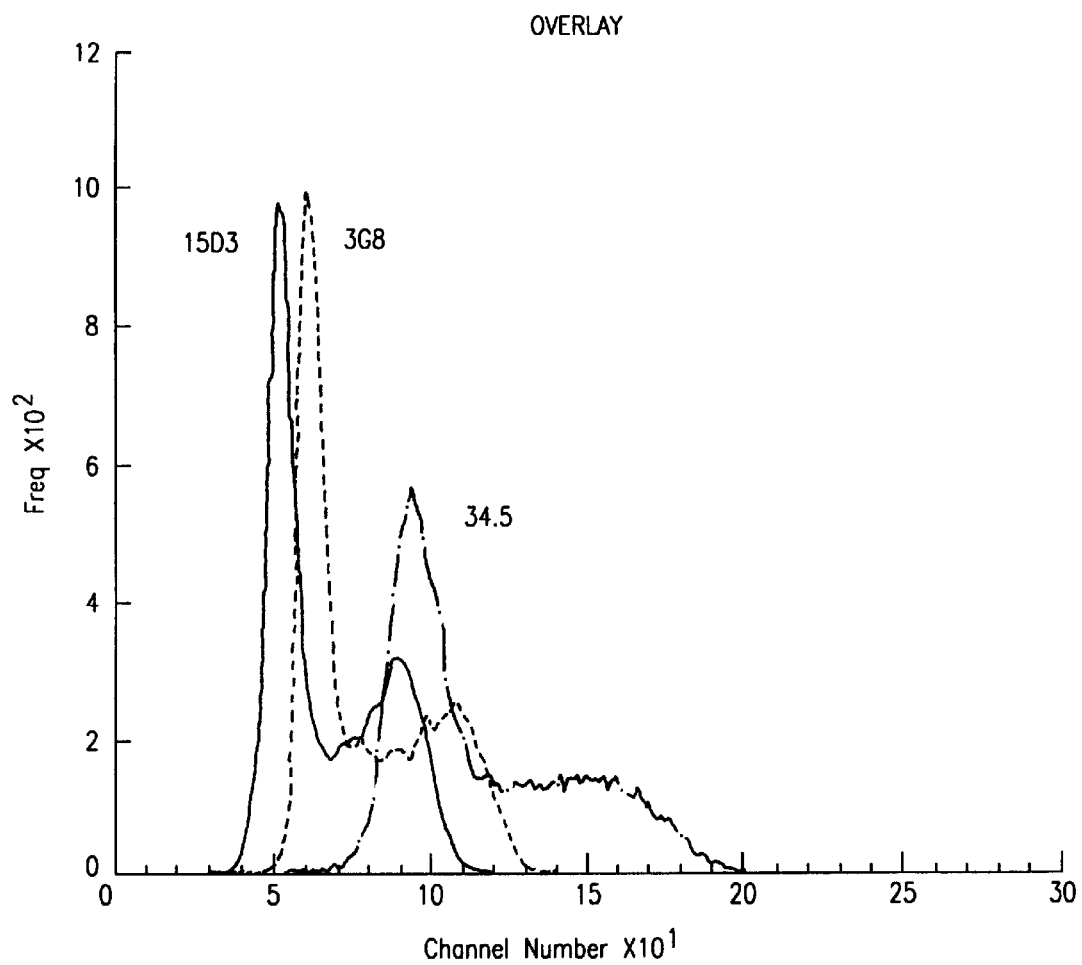
FIG. 2 presents the DNA staining of parental hybridomas 3G8 and 15D3 and of hybrid hybridoma 34.5.

The invention described herein draws on previously published work and pending patent applications. By way of example, such work consists of scientific papers, patents or pending patent applications. All of these publications and applications, cited previously or below are hereby incorporated by reference.

The bispecific antibodies disclosed herein have the following advantages. They can promote the efficacy of a cytotoxic cell by positioning it against a cell target to be destroyed. This is achieved by an antibody binding through one of its binding sites to an antigen on the target cell and through the second binding site to a lysis promoting Fc receptor on the cytotoxic cell thereby joining the two cell types (cross-linking) and causing the cytotoxic cell to deliver a lethal hit.

Specifically, this invention presents hybrid hybridomas and the bispecific antibodies produced by them, which are capable of cross-linking human Fc receptor-bearing immune effector cells and antigens expressed on tumor cells. Examples of the Fc receptor-bearing effector cells are macrophages, neutrophils, eosinophils, NK cells and large granular lymphocytes. The preferred effector cells are cytotoxic cells. Preferably, the bispecific antibodies recognize Fcγ receptor. The preferred Fcγ receptor is hFcγRIII on human and chimpanzee leukocytes. More preferably, the bispecific antibodies also recognize MDR antigens on tumor cells. Also disclosed in this invention are parental hybridomas which produce MABs targeted to cells expressing the MDR phenotype. The most preferred MDR antigen is P-glycoprotein.

The cell lines used in the present invention may be cell lines of diverse mammalian origin. For example, rodents (e.g., rat, mouse, hamster), primate and human embodiments are contemplated, with human and murine embodiments being illustrated in the examples which follow. The antibodies may be of any class, the IgG/IgG type being specifically exemplified herein.

The preferred hybrid hybridomas are formed from the fusions of parental hybridomas which produce antibodies recognizing FcRs on cytotoxic effector cells and MDR antigens on tumor cells. The hybrid hybridoma specifically exemplified is a hybrid hybridoma 15D3/3G8 which resulted from the fusions of the preferred hybridomas 15D3 and 3G8. Hereinafter, the MAB or bispecific antibody produced by a particular hybridoma or hybrid hybridoma clone will share the same designation as the hybridoma or hybrid hybridoma clone. For example, "bispecific antibody 34.5" denotes the bispecific antibody produced by clone 34.5.

The hybrid hybridomas can be grown for the production of the bispecific antibodies, in various media using various techniques known in the art. (See for example: Freshney, R. I. (2d ed. 1987), *Culture of Animal Cells: A Manual of Basic Technique*, New York, Alan R. Liss).

The derivation and characterization of MDR sublines of human KB carcinoma cells are described in Akiyama et al., 1985, *Somat. Cell Mol. Genet.* 11:117; Fojo et al., 1985, *Cancer Res.* 45:3002 and 1985, *PNAS (USA)*, 82:7661; Reichert et al., 1985, *PNAS (USA)* 82:2330; Shen et al., 1986, *Science*, 232:643. In the following examples, KB-3-1 is the parental non-drug resistant cell line. KB-A1, KB-C1, and KB-V1 are subclones selected in 1 μg/ml of adriamycin, colchicine, and vinblastine respectively.

The drug resistant human cell lines and their parental non-drug resistant cell lines used in the following Examples are described below.

TABLE 1

| Cell Lines | Cell Type | Selecting Drug | Drug Concentration in Culture |
|---|---|---|---|
| KB-3-1 | Human colon carcinoma | — | — |
| KB-A1 | Human colon carcinoma | Adriamycin | 1 μg/ml |
| KB-C1 | Human colon carcinoma | Colchicine | 1 μg/ml |
| KB-V1 | Human colon carcinoma | Vinblastine | 1 μg/ml |
| K562 | Human myelogenous leukemia | — | — |

TABLE 1-continued

| Cell Lines | Cell Type | Selecting Drug | Drug Concentration in Culture |
|---|---|---|---|
| K562/R7 | Human myelogenous leukemia | Adriamycin | 1 µg/ml |
| K562/V.2 | Human myelogenous leukemia | Vinblastine | 0.2 µg/ml |
| MES-SA | Human fibroblast sarcoma | — | — |
| MES-DX5 | human fibroblast sarcoma | Adriamycin | 0.5 µg/ml |

The production of these hybrid hybridomas and bispecific antibodies involves: production of the parental hybridomas; fusion of the parental hybridomas; selection of the hybrid cells (in this case hybrid hybridomas); selection of the hybrid hybridomas secreting the desired bispecific antibodies; and purification of the bispecific antibodies. The general procedures described below.

1. Labelling the Parental Hybridomas

The initial step in the identification and isolation of hybrid cells by the methods of this invention involves incubating, in a suitable physiological solution, those cells which are to be fused. The procedure can be carried out in a plate (plate fusion method) or a test tube (tube fusion method). The following describes a general tube fusion method. An example of a plate fusion method is described in U.S. Pat. No. 4,677,070, to Larrick et al., issued Jun. 30, 1987, "Pseudomonas Aeruginosa Exotoxin A Antibodies, Their Preparation and Use." The following "Examples" section also describes the specific plate fusion method used in this invention. The general concept of the tube fusion method applies to the plate fusion method, and one skilled in the art could modify it to apply to the plate fusion method. In the tube fusion method, the cells to be fused are in separate tubes, instead of plates. One of the tubes contains the fluorescent dye of choice. The cells in the tube containing the fluorescent dye are allowed to incubate until an amount of fluorescent dye is taken up which is sufficient to be subsequently detected in a hybrid.

A wide variety of physiological solutions can be used to incubate cells in the presence of the fluorescent dye. For instance, the cells can be incubated for short periods of time in physiological solutions lacking nutrients, such as phosphate buffered saline, or if a particular fluorescent dye requires longer incubation times to effect uptake of detectable amounts of dye, then the cell line is more appropriately incubated in a solution supplemented with nutrients, preferably cell culture media, to prevent cellular deterioration. The pH of the solution is expected to be in the range of about 7.4; however, variations are anticipated to be usable that do not significantly affect the uptake of the fluorescent dyes, nor adversely affect the viability of the cells.

The concentrations of the fluorescent dyes in the labeling solution must be non-toxic to the cells, yet high enough for the cells to take up an amount that can be detected in hybrids using the fluorescence activated cell sorter after the cells are fused and hybrids formed.

The effect of fluorescent dyes on cell viability can be measured using techniques well known to those skilled in the art. A most useful technique is described by Mosmann, T., 1983, *J. of Immunol. Methods,* 65:55, which measures cell viability as a function of cell number. Thus, the effect of fluorescent dyes on both cell viability and cell number can be measured simultaneously. The assay is based on the conversion of colorless tetrazolium salts by mitochondrial dehydrogenase enzymes to a detectable colored product. A favored tetrazolium salt is MTT, or (3-(4,5-dimethylthylthiazol-2-yl)-2,5-diphenyl tetrazolium bromide).

Examples of fluorescent dyes that can be used are rhodamine 123 and hydroethidine. Rodent cells, particularly mouse cells, exhibit a high efflux rate for rhodamine 123. However, when the cells are incubated with rhodamine 123 and verapamil, then rhodamine 123 is maintained inside the cells for a longer period than if verapamil is absent. Verapamil is commercially available from Sigma Chemical Corp., St. Louis, Mo. The effective concentration of verapamil can be determined empirically using techniques known in the art. Without wishing to be bound by the following postulation, it is postulated that P-glycoprotein plays a role in removing rhodamine 123 from inside the cells. Therefore, chemicals which inhibit this activity of P-glycoprotein would assist in maintaining the rhodamine 123 in the cells. Examples of such chemicals are: diltiazem, quinidine, and reserpine (Pastan, I. et al., 1987, *New England J. Med.,* 316:1388).

For most dyes the concentration employed will be in the µg/ml range, and preferably in the range of 0.1–20 µg/ml. The preferred dye is rhodamine 123. Hydroethidine and rhodamine 123 are preferably used at concentrations of about 0.1–10 µg/ml and 1–15 µg/ml, respectively. The most preferred concentrations of these dyes are 0.25–0.5 µg/ml for rhodamine 123, and 5–10 µg/ml for hydroethidine.

Other details regarding labeling of cells with suitable fluorescent dyes are the optimal time that the cells should be incubated with the dyes, as well as the incubation temperature. The labelling period can vary considerably depending on the cell types used, as well as the concentration of the fluorescent dyes. However, the preferred incubation period is about 10–50 minutes, more preferred is 15–30 minutes, most preferred is 20 minutes. The cells can be incubated at various temperatures, which will in turn affect the incubation period. The optimal time for the various parameters can be determined empirically. However, for both rhodamine 123 and hydroethidine, the preferred incubation temperature for cells incubated 20 minutes is about 37° C. After the cell lines are labelled with the appropriate fluorescent dye, they are washed to remove residual dye and incubated in a physiological solution, preferably cell culture media, in preparation for carrying out the cell fusion procedures described below.

In the preferred method, the first step in the fusion process is to label one of the parental hybridomas with a fluorescent dye. This preferred method has an advantage over the prior art in that it utilizes a single dye for labelling one of the parental hybridomas. The prior art utilizes two dyes, each labelling one parental hybridoma. Since the dyes are toxic to the cells, the preferred method disclosed herein has the advantage of reduced cell death and thus produces a higher yield of hybrid hybridoma per fusion run.

2. Cell Fusion

The fusion of two parental hybridomas to form a hybrid can be conducted using techniques known in the art, for example, that which is disclosed in U.S. Pat. No. 4,474,893, to Reading, C. L., supra.

The cell line containing the appropriate fluorescent dye is combined with the unlabelled cell line fusion partner, in a physiologically acceptable solution, and fused using standard cell fusion materials and methods. It is important to note that regardless of the procedure used, in those instances where the cell lines employed exhibit a significant rate of efflux of, for example, rhodamine 123 from rodent cells, that the fusing mixture will contain a suitable inhibitor of P-glycoprotein activity, preferably verapamil. Fusion can be effected using a variety of fusogens, the preferred fusogen, however, is polyethylene glycol. More preferred are polyethylene glycols having molecular weights in the range of 1500 to 4000. The most preferred is polyethylene glycols having a molecular weight of 4000. Thus, the ratio of the labelled cell line to the nonlabelled cell line should be in the vicinity of 1 to 10–20. The labelled cell line can be at any concentration, however, it is preferred that about $10^6$–$10^7$ cells of the labelled cell line be utilized.

More specifically, the fusion procedure consists of combining about $10^6$–$10^7$ cells of the labelled cell line with about $10^7$–$2\times10^8$ of the unlabelled cell line in a suitable cell culture media, with or without verapamil depending on the type of cell lines fused. The cell mixture is centrifuged to pack the cells, and the cells fused using polyethylene glycol 4000. The technique employed is described by Kohler and Milstein, 1975, *Nature,* 256:495. Briefly, one procedure whereby cell hybridization can be achieved is by the addition of 0.5 ml of a 50% (v/v) solution of polyethylene glycol 4000 dropwise over 30 seconds at room temperature, followed by a 30 second incubation at 37° C. The cell suspension is slowly mixed with the addition of 20 ml of cell culture media containing 10% fetal calf serum. Next, cells are gently resuspended in cell culture medium containing 10% fetal calf serum and incubated for 2–4 hours at 37° C. prior to sorting the cells using a fluorescent activated cell sorter equipped with an argon laser that emits light at 488 or 514 mm. These wavelengths are particularly useful when hydroethidine or rhodamine 123 dye is used. Hydroethidine is converted intracellularly to ethidium, which when excited at either 488 or 514 mm emits a red fluorescence. In contrast, rhodamine 123 emits a green fluorescence when excited at either wavelength.

Thus, if one parental cell is incubated with hydroethidine while the other is incubated with rhodamine 123, the resulting hybrid cell will emit both red and green fluorescence at either 488 or 514 mm wavelength. If only one of the parental cells is incubated with either of the dyes, depending on the dye used, the resulting hybrid cell will either emit red (for hydroethidine) or green (for rhodamine 123) fluorescence.

3. Cell Sorting

Hybrids present in the mixture of fused cells can be isolated using a fluorescence activated cell sorter (hereinafter referred to as FACS). While a variety of such machines are available, we have found that a Coulter EPICS V, or a FACS III Cell Sorter produced by Beckon-Dickinson, Sunnyvale, Calif., perform adequately. Both are equipped with argon ion lasers. The laser is preferably used at a power setting of about 150 mW, and as mentioned above, at an excitation wavelength of 488, or 514 mm. Standard minors and filters are employed to be compatible with, and to collect the fluorescence emitted by, the select fluorescent dyes. Similarly, standard techniques are used to set the cell sort windows that are used to select the hybrid cells, and are described by L. Karawajew, B. Michael, O. Behrsing and M. Gaestel, 1987, *J. Immunol. Methods,* 96:265–270. Where only one parental cell has been dyed, the resulting hybrids can be selected on the basis of their exhibiting the correct fluorescence, and their size or DNA content. The hybrids should be bigger and have more DNA content than either parental cells. Methods and materials for determining the size and DNA content of cells are known in the art, examples of which are shown in Examples 2 and 7, below.

4. Identification of Antibody Secreting Hybrid Hybridomas

As mentioned above, the instant technique is particularly useful to isolate antibody secreting hybrid cells, preferably triomas and hybrid hybridomas. However, because not all hybrid cells isolated by fluorescence activated cell sorting will secrete antibody, those that do must be identified. As applied to detecting hybridomas, the most general approach involves assaying medium for antibody secreted by hybrid cells using a solid phase assay, although other techniques are known that can be used. Similar techniques are available to detect membrane, or non-soluble antigens. In both instances, antigen is bound to a solid support, the support treated with a suitable blocking agent, and antigen detected either directly with labeled hybridoma antibody, or indirectly with a labeled molecule that binds to hybridoma antibody. The latter can be antibody, protein A, or other suitable binding agents. Such assays are known in the art, and are shown by Langone, J. and Van Vinakis, H., *Methods of Enzymology,* 92, Part E (1983). Antibody secreted by triomas or hybrid hybridomas can be identified by the methods described above, but additional assays may be performed to ascertain the bi-functional characteristics and properties of the antibody. As discussed above, triomas or hybrid hybridomas may produce antibody that is bispecific. Antigen binding may be simultaneous or sequential. In order to confirm that triomas or hybrid hybridomas can be isolated by the instant techniques, antibody secreted by these cell lines can be characterized by any functional test which depends upon the binding of two different antigens by the same antibody molecule.

For example, bispecific antibody can be identified using bi-functional antigen screening assays to establish that the antibody does indeed recognize two distinct antigens, and thus is composed of two different antigen binding sites. Such assays are also known in the art, an example of which is described in U.S. Pat. No. 4,474,893 to Reading, C. L., supra. U.S. Pat. No. 4,474,893 also present methods for making and identifying hybrid hybridomas.

If the bispecific antibody is designed to target cytotoxic cells to trigger cytotoxicity, cellular cytotoxicity assays can be employed to identify the antibody secreted. Cellular cytotoxicity is thought to involve cell surface receptors on cytotoxic cells, such as monocytes, macrophages, NK cells etc. These receptors are thought to be specific for, and to interact with membrane components on a target cell, thereby causing cell lysis by forming conjugates between the cytotoxic cell and the target cell. If the cytotoxic cell is positioned up against the target cell, cytotoxicity is enhanced. Bispecific antibody can promote this process by binding to a target cell through one of its combining sites, and to the lysis promoting receptor on the cytotoxic cell through the second combining site, thereby joining the two cell types and causing the cytotoxic cell to deliver a lethal hit. The materials and methods for performing these assays are generally known to those skilled in the art. Representative assays are described by Mishell and Shiigi, in *Selected Methods in Cellular Immunology,* p.130, eds. C. Henry and R. Mishell, publisher W. H. Freeman and Co., San Francisco (1984), and later Herlyn D. et al., "Monoclonal Anti-Human Tumor Antibodies of Six Isotypes in Cytotoxic Reactions with Human and Murine Effector Cells", *Cellular Immunol,* 1985, 92:105–114. The former reference describes a $^{51}$Cr release assay, whereas the latter reference shows a $^3$H release assay involving measuring the release of tritiated thymidine from lysed cells.

5. Purification of Antibody

After the triomas or hybrid hybridomas have been identified using functional assays as referred to above, the bispecific nature of the antibody can be confirmed by determining the composition of isolated antibody preparations. Bispecific antibody should be composed of light and heavy chains of both fusing partners. Antibody can be purified from culture media or body fluids, as the case may be, by conventional immunoglobulin purification procedures such as ammonium sulfate precipitation, gel electrophoresis, dialysis, chromatography, and ultrafiltration, if desired. Ion exchange, size exclusion hydroxylapatite, or hydrophobic interaction chromatography can be employed, either alone or in combination. Light and heavy chain analysis can be carried out using gel electrophoretic techniques or isoelectric focusing, as well as other techniques known in the art.

6. Composition of Effector Cells Armed with Bispecific Antibodies

The bispecific antibodies presented in this application can be used in medical treatment, for example, in a composition comprising a physiologically acceptable carrier. (Hereinafter referred to as the bispecific antibody treatment regimen and the bispecific antibody composition.) Alternatively, the bispecific antibodies can be presented in an armed effector cell composition. More specifically, the armed effector cell composition comprises effector, more preferably cytotoxic cells, expressing hFcγRIII dispersed in a physiologically acceptable carrier; the effector, or more preferably, cytotoxic cells being armed (bound) with bispecific antibodies which recognize both the hFcγRIII and MDR markers. The preferred MDR marker is P-glycoprotein. The preferred target cells are tumor cells which over-express P-glycoprotein as compared to normal cells. The armed effector or cytotoxic cells are in an amount effective to kill the target cells.

For example, a leukocyte population such as total mononuclear cells (TMCs) that contain cytotoxic cells expressing hFcγRIII could be used. A variety of methods for obtaining the TMCs could be used, for example, as described in the examples below. The leukocytes utilized can be obtained from whole blood without further separation into more narrowly defined cell populations. More specific leukocyte sub-populations, such as NK cells or monocytes/macrophages, can be obtained using methods known in the art, for example, as described in *Cellular Immunology*, 2: 24.1, (Weir, D. M. ed.) 1979, Blackwell Scientific Publications, United Kingdom. The leukocytes utilized can be autologous, i.e., from the same animal as the tumor cells, or can be from another compatible animal provided the cells do not elicit adverse immunological response when administered to the recipient animal.

The leukocytes are cultured ex vivo under cell culture conditions known in the art. The armed effector cells are formed by admixing the effector cells with an effective amount of bispecific antibodies, preferably those presented in this patent application, for a period of time sufficient for the binding of the antibodies to the effector cells. To optimize the binding, an excess of the bispecific antibodies is normally used. The bispecific antibodies are preferably purified before use. The purification can be achieved by a number of methods known in the art. The typical admixture, contact, and maintenance (co-incubation) times and experimental conditions for arming the effector cells with the bispecific antibodies can be determined by one skilled in the art without undue experimentation.

An effective amount of the resulting armed effector cells can be dispersed in a physiologically acceptable carrier. Examples of physiologically acceptable carriers include normal saline, PBS, Ringer's solution, or lactated Ringer's solution. The resulting armed effector cell composition can be used to lyse target cells in vivo or in vitro. The effective cytotoxic amount of the armed effector cells can vary between in vitro and in vivo uses, and taking into consideration factors such as the amount of target cells, target cell type, the particular assay used and the contact time and temperature.

For in vitro cytotoxicity, the preferred effector to target cell ratio is about 5:1 to about 500:1, more preferably the ratio is about 25:1 to about 100:1. For in vivo cytotoxicity, about $1 \times 10^4$ to about $1 \times 10^{10}$, and more preferably about $1 \times 10^6$ to $1 \times 10^9$ armed effector cells, calculated as a TMC population, are useful for adult human. Such cells are typically prepared using about 200–400 µg of purified bispecific antibody per about $1 \times 10^7$ to about $2 \times 10^7$ effector cells.

Further, before arming the effector cells with the bispecific antibodies, the effector cells can be activated with one or more activating factor(s) which have the effect of stimulating the cytotoxic activity, growth or production of the effector cells. Examples of such activating factors are: interleukin-2 (IL-2) and macrophage colony-stimulating factor (M-CSF). The phenomenon wherein lymphocytes are activated by lymphokines to kill target cells is called lymphokine-activated killer (LAK) activity. The general method for activating the effector cells with IL-2 is described in U.S. Pat. No. 4,844,893, Jul. 4, 1989, to Honsik et al., "Ex Vivo Effector Cell Activation for Target Cell Killing". M-CSF promotes the production of FcγRIII cells, antibody-dependent cellular cytotoxicity (ADCC) development and increased in ADCC activity in monocyte culture, see Young, D. A. et al., *J. Immun.*, 145: 607, "Comparison of the Effects of IL-3, Granulocyte-Macrophage Colony-Stimulating Factor, and Macrophage Colony-Stimulating Factor in Supporting Monocyte Differentiation in Culture." Alternatively, in treatment regimens involving the armed effector cell composition or the bispecific antibody composition, the activating factor(s) can be administered either separately from, or as part of the armed effector cell composition or bispecific antibody composition. For the method of administering LAK cells and IL-2, see for example, Riddell, S., et al., 1988, in *ISI Atlas of Science: Immunology*, 1:175, Institute of Scientific Information, PA, U.S.A. The method described therein can be modified by one skilled in the art to use in combination with the bispecific antibody or armed effector cell composition described in this patent application. The composition, with or without the activating factor, can be administered according to the method set forth in Example 12 below.

Having generally described the invention, examples illustrative of its application will now be presented. However, it will be understood by those skilled in the art that the examples are not intended to be restrictive in any way of the invention.

Although any similar or equivalent methods and materials may be employed in the practice or testing of the present invention, the preferred methods and materials are now described. Two hybrid hybridoma clones that produced bispecific antibodies were selected from fusion of the parental hybridomas 15D3 and 3G8. In an in vitro cytotoxicity assay, these bispecific antibodies could cross-link hFcγRIII-bearing NK cells with human MDR-positive K562/R7 tumor cells to promote specific lysis of the tumor cells.

Because these 15D3/3G8 hybrid hybridomas were formed by fusion of the parental hybridomas 15D3 and 3G8, and selected therefrom, the order of discussion of the invention will be: production of parental hybridoma 15D3; testing of antibodies produced by parental hybridoma 15D3 for binding; testing of antibodies produced by parental hybridoma 3G8 for binding to hFcγRIII positive cells (human PMNs); fusion of 15D3 and 3G8 to obtain 15D3/3G8 hybrid hybridomas; cloning of 15D3/3G8 hybrid hybridomas; testing of target MES-DX5 cells for MDR antigens (through binding of anti-MDR antibodies to the MES-DX5 cells); screening of 15D3/3G8 hybrid hybridoma clones using anti-MDR live cell Enzyme-Linked Immunosorbent Assay (ELISA), using target MES-DX5 cells; anti-MDR/hFcγRIII bridge assay of the bispecific antibody produced by the 15D3/3G8 hybrid hybridomas; DNA analysis of the 15D3/3G8 hybrid hybridoma clones; assay for 15D3/3G8 bispecific antibodies' specific binding for MDR cells (P-glycoprotein positive K562/R7) and hFcγRIII positive cells (human PMNs); collection and purification of the bispecific antibodies; assay of the purified bispecific antibodies for cytotoxic targeting activity, sub-cloning of the 15D3/3G8 hybrid hybridomas for stable hybrid hybridoma clones, and medical treatments using the 15D3/3G8 bispecific antibody.

EXAMPLE 1

Making of Parental Hybridoma 15D3

A. Procedure

1. Immunization

Murine fibroblast cell lines were used as live whole cell immunogens. These cell lines were obtained from Dr. Igor Roninson at the University of Illinois, Chicago Medical Center. The cell lines were Balb/c 3T3 fibroblast cells, which were transfected with the human MDR1 gene and then selected for the drug resistance phenotype by growing them in vinblastine-containing culture medium (designated BATV.2 to indicate that the cells had been grown in and were resistant to 0.2 μg/ml of vinblastine drug). For immunizations, five million live drug resistant cells were inoculated intra-peritoneally into six-week old male Balb/c mice, which had been injected intra-peritoneally with thirty million drug-sensitive parent 3T3 fibroblast cells (BA3T3) 24 hours after birth to induce neonatal tolerization against parent cell antigens. The adult mice were boosted at two-week and six-week intervals, by intra-peritoneal injections with five million BATV.2 cells. Three days after the last intravenous boost, the spleens were removed for cell fusion.

2. Fusion of Cells and Cloning of Hybridomas

Somatic cell hybrids were prepared by the method of Buck, D. W., et al., 1982, *In Vitro*, 18:377–381, using the azaguanine resistant, non-secreting murine myeloma cell line SP2/0-Ag14 (obtained from the American Type Culture Collection, designated under cell repository line number ATCC CRL1581). 96-well polystyrene flat-bottom microtiter plates were used. One thousand five hundred wells were generated from those fusions, of which one thousand and fifty exhibited hybridoma growth.

3. Assay of Monoclonal Antibodies

The hybridoma supernatants were assayed for reactive antibody in either a solid phase ELISA or an indirect immunofluorescence assay both with the immunizing BATV.2 cell line and the parent BA3T3 cell line. For the solid phase ELISA, each 96-well polyvinylchloride (PVC) flat-bottom microtiter plate was coated with 50 μl per well of a prewashed cell suspension at $2 \times 10^6$ viable cells/well. Plates were centrifuged for 5 minutes at 900×g. To each well was added 50 μl of 0.5% glutaraldehyde in cold phosphate buffered saline (PBS) and incubated for 15 minutes at room temperature. The cells were then washed twice in PBS and filled with 100 mM glycine in 0.1% bovine serum albumin (BSA) for 30 minutes at room temperature. After washing twice with PBS, the wells were incubated with 50 μl of hybridoma supernatant (either neat or diluted) for 1 hour at room temperature. After washing three times with PBS, 100 μl of a 1:200 dilution of peroxidase-conjugated goat anti-mouse IgG was added to each well. The diluent was PBS with 0.1% BSA. The wells were then washed with PBS and reacted with 100 μl of O-phenylenediamine substrate (0.5 mg/ml in 0.1 M citrate buffer pH 6.5 with 0.5 μl/ml $H_2O_2$) for 5 to 15 minutes at room temperature. The reaction was quenched with 100 μl of 1N HCl. Optical density was measured at 495 nm on a Micro-ELISA reader (Flow Lab., Inc., McLean, Va.). The background was 0.1±0.1 optical density units using medium without mouse monoclonal antibody. Wells that gave a reaction on the BATV.2 cells that was at least 2-fold greater than the reaction with BA3T3 cells were saved for cloning. 6.7% of all the hybridomas tested were saved for cloning.

Clones from the hybridomas selected by the solid phase ELISA assay were then subjected to indirect immunofluorescence cell line assay. 100,000 BATV.2 cells of the immunizing cell line (and other drug-resistant lines) were seeded overnight with appropriate medium in each chamber of a set of 8 chambered slides. The other drug-resistant cell lines were: KB-A1, KB-C1, and KB-V1. The parental cell line KB-3-1 which was sensitive to all three drugs was also used. The KB-A1, KB-C1, and KB-V1 cell lines were obtained from Ira Pastan of National Cancer Institute (NCI) of the National Institute of Health (NIH), Bethesda, Md. The cells were washed with PBS containing 0.1% BSA. The slides of either cell type were incubated with 1:10 dilutions of hybridoma supernatant for 30 minutes at 4° C. The cells were again washed and incubated at 4° C. for 30 minutes with a 1:50 dilution of fluorescein isothiocyanate (FITC)-conjugated goat F(ab')$_2$ anti-mouse IG. The cells were washed three times, fixed in 1.5% formaldehyde in PBS for 5 minutes, and the chambers were removed and the slides were rinsed in PBS. The slides were then mounted and examined with a fluorescence microscope. Hybridomas which produced MABs that showed strong fluorescent binding to drug-resistant cells but little or no detectable fluorescent binding to drug-sensitive cells were saved.

B. Result

Thirteen hybridoma wells revealed such specificity in this screen. These wells gave a reaction on the resistant cell lines that was at least 2-fold greater than the reaction with the KB-3-1 cells. Hybridoma 15D3 was selected from one of these thirteen wells.

EXAMPLE 2

Labelling of Cells with Fluorescent Dyes

A. Procedure

The PEG fusion mixture contained 40% polyethylene glycol (PEG) 4000 (BDH Chemicals, Poole, England); 10% (v/v) dimethylsulfoxide (DMSO), and 10 μM verapamil in HBSS −/+ (Hank's Balanced Saline Solution without $Ca^{2+}$ but with 2 mM $Mg^{2+}$). The mixture was heated at 56° C. for 1 hour to dissolve the PEG. Before use, the pH of the resulting solution was adjusted to between 7.5 to 8.0 with sterile 0.1N NaOH, and filtered through a 0.45μ millipore filter. The fusion dilution medium (FDM) contained HBSS−/+, 5% DMSO (Sigma Chemical Co., supra) and 10 μM verapamil (filter sterilized).

To a 6 well-plate (35 mm well diameter) were added 1.5 ml of HBSS −/+ and 20 μl peanut agglutinin (PNA from stock solution of 100 μg/ml of PNA in HBSS −/+ from Sigma Chemical Co., supra). The PNA stock was stored at −20° C., and a freshly thawed aliquot was used to coat the fusion plates. Before fusion, the plates were incubated 2 hours at 37° C.

The 3G8 and 15D3 hybridomas were washed with HBSS −/+ twice. Then the 3G8 cells were stained with rhodamine 123 at 4 μg/ml in the presence of 10 μM verapamil, at 37° C. for 10 minutes. At the end of 10 minutes, the 3G8 cells were thrice washed with HBSS −/+ containing verapamil.

The stained 3G8 cells were mixed with 15D3 cells at a ratio of 1:20 in a 50 ml centrifuge tube and the mixture was centrifuged at 400×g for 5 minutes at room temperature to form a tight pellet. At most $2 \times 10^7$ cells were resuspended in 2 ml and added to the pretreated 6-well plate. The cells were spun into the plate at 400–500×g for 6 minutes (1400 rpm). The supernatant was then aspirated off the monolayer. Two ml of warmed 37° C. PEG fusion mixture was added down the side of each well and the plate was swirled once or twice. After 2 minutes, FDM at 37° C. (or room temperature) was added at 2 ml/minute to the constantly swirled 6-well plate. The procedure was repeated with gentle rocking of the 6-well plate. Then the supernatant was aspirated from the wells. FDM at 37° C. was twice added at 5 ml/minute into the 6-well plate, and the mixture in the well aspirated.

Five ml of HBSS −/+ at 37° C. was added per well to the 6-well plate. The plate was spun at 400–500×g for 1 minute (at 1400 rpm). The speed was brought up gently. The supernatant was then aspirated. The 6-well plate was twice washed with 5 ml of HBSS −/+, with aspiration of the supernatant in between. Then at most 5 ml of 15% fetal calf serum (FCS) complete medium was added to the 6-well plate. The cells were incubated at 37° C. for 4 hours.

The cells were sorted by means of autoclone cell sorter at 488 nm, 150 MW, 488 LB, 525 BP. (LB designates laser blocking and BP designates Band Pass) The cells were sorted based on their sizes using Forward Angle Light Scatter (FALS). Only fluorescent large cells as shown by their higher FALS, were selected and sorted into a 12 well plate (about 5,000 cells in a single well).

5,000 cells were sorted and incubated at 37° C. for 18 hours before being cloned into a 96-well plate at 1 cell/well. Since only 3G8 cells were stained and they were fused with 15D3 cells at a ratio of 1:20, most of the sorted cells were either 3G8 or 15D3/3G8 fused cells.

B. Result

The result showed that 4.1% of the cells were selected on the basis of green fluorescence; next, 3.89% of the green fluorescent cells were selected based on their large size. The combination of fluorescence and size selection resulted in 0.41% of the total cell population being selected after fusion.

EXAMPLE 3

Cloning of 15D3/3G8 Quadromas

The fused cells obtained from Example 2 were suspended in Iscove's medium with 15% fetal bovine serum (FBS) to reach a final concentration of 10 cells/ml. These cells were then plated onto fifty 96-well round-bottom plates (1 cell/100 μl/well). Iscove's medium containing 15% FBS (100 μl/well) was added to the plates and the cells were incubated for 15–21 days at 37° C., 5% $CO_2$. Next, the plates were screened for growing clones. The growing clones were screened by means of an anti-MDR live cell ELISA assay. The target cells in this anti-MDR live cell ELISA assay were MES-DX5.

EXAMPLE 4

Testing of Target MES-DX5 cells for MDR Markers Through Binding of Anti-MDR Antibodies to the MES-DX5 Cells The MES-DX5 and MES-SA cells are MDR-positive and MDR-negative human fibroblast sarcoma cells, respectively.

Both cell lines were obtained from Dr. B. Sikic of Stanford University, Palo Alto, Calif. Before the MES-DX5 cells could be used for screening the 15D3/3G8 bispecific antibody, the following experiment was conducted which confirmed that anti-MDR antibody would bind to the MES-DX5 cells, whereas an irrelevant (non-anti-MDR) antibody would not. Further, the experiment also showed that the anti-MDR antibody would not bind to MES-SA cells. The MES-SA cells served as the negative control. The negative control for the antibody was a mouse myeloma protein of the IgG1 class, denoted MOPC21, which does not bind P-glycoprotein or any known antigen.

A. Procedure

The MES-DX5 and MES-SA cells were twice washed with HBSS −/− (Hank's Balanced Salt Solution without $Ca^{2+}$ and $Mg^{2+}$) (JR Scientific, Woodland, Calif.). Trypsin-EDTA (6.25% trypsin (w/v), 1/20,000 EDTA (w/v), in HBSS −/−) was then added to the cells. The cells were collected, spun and then suspended in Iscove's medium with 10% FBS. The suspended cells were seeded into 96 well flat-bottom microtiter plates at final concentration of 30,000 cells/100 μl/well, and incubated at 37° C., 5% $CO_2$, for 20 hours. Next, the supernatant was aspirated. To the resulting supernatant, purified MDR-positive 15D3 and 17F9 supernatant were respectively added to serve as positive controls (17F9 is a monoclonal anti-MDR antibody obtained by the same procedure as 15D3 in Example 1). In another study, MOPC21 was added as a negative control. The mixtures were incubated at room temperature. After 60 minutes, the supernatant of each sample was aspirated, the cells were washed thrice with 200 μl/well of PBS containing 1% BSA (hereafter referred to as PBS-BSA). Then 100 μl/well of 2.5 μg/ml rabbit anti-mouse IgA, IgG and IgM conjugated with peroxidase (hereinafter referred to as "RAM-peroxidase") was added to the wells, and the cells were incubated at 4° C. for 30 minutes. The supernatant was aspirated and the cells were washed thrice with PBS-BSA in order to remove the free antibodies. To each well was added 150 μl/well of substrate at 37° C., for 30 minutes. The substrate consisted of 0.5 mg/ml of ABTS (2,2'-Azinobis (3-ethylbenzthiazolinesulfonic acid)) (Sigma Chemical Co., supra) in 0.1 M Na Citrate, pH 4.5—to which 30% $H_2O_2$ at 1:100 dilution was added just before the substrate was added into the plate.

B. Result

The ELISA reading showed no specific binding of MABs 17F9 or 15D3 to MES-SA cells. The negative control (MOPC21) gave a similar background reading. The titration results of the antibodies binding to MES-DX5 cells showed that MOPC21 gave a very low background. In contrast, MAB 17F9 gave a high OD even at 1:32 dilution. MAB 15D3 gave an OD reading about halfway between that of 17F9 and MOPC21.

EXAMPLE 5

Screening of 15D3/3G8 Hybrid Hybridoma Clones Using Anti-MDR Live Cell ELISA, With MES-DX5 Cells as Targets In the following experiment, the hybrid hybridomas obtained from Example 3 were selected for their ability to produce anti-MDR antibody. The target cells used were human MES-DX5. 15D3 supernatant was used as a positive control. The negative control antibodies were MOPC21, 3G8 and RAM-peroxidase without primary antibody.

A. Procedure

The MES-DX5 cells were twice washed with HBSS −/−. Next, trypsin-EDTA (6.25% trypsin (w/v), 1/20,000 EDTA (w/v), in HBSS –/– was added to the cells. The cells were collected, spun, resuspended in Iscove's medium with 10% FBS. The cells were seeded into 96-well microtiter plates at a final concentration of 30,000 to 50,000 cells/100 μl/well, at 37° C., 5% $CO_2$, for 48 hours. The supernatant fluid from the cells was aspirated. To the cells was added 50 μl/well of the 15D3 (positive control), MOPC21, 3G8 supernatant or medium alone (negative controls), respectively. The cells were incubated at room temperature for 60 minutes. The supernatant was aspirated and the cells washed thrice with PBS-BSA. 100 μl/well of RAM-peroxidase without primary antibody (2.5 μg/ml) was then added. The cells were incubated at 4° C. for 30 minutes. The supernatant was again aspirated, and the cells washed thrice with PBS-BSA. ABTS (at 0.5 mg/ml in 0.1 M Na Citrate, pH 4.5 with the addition of 30% $H_2O_2$ at 1:100 dilution just before addition to the plate) was then added at 150 μl/well and the cells were incubated at 37° C. for 30 minutes.

B. Result

The anti-MDR live cell ELISA assay showed basically no non-specific binding (–0.002±0.009) for the myeloma protein MOPC21 (negative control). The RAM-peroxidase alone gave an OD reading of 0.010±0.009. The 3G8 supernatant did not provide any specific binding (its OD reading was –0.009±0.023). At the OD reading of 0.424±0.060, the positive control 15D3 supernatant was 20-fold higher than the negative control.

Among the 160 clones screened after 15 days of fusion, 13 showed an OD reading above 0.05 (with a range of 0.053 to 0.185). The slow growing clones were tested 19 days after fusion. Seven of the 160 slow growing clones showed an OD reading above 0.05 (with a range of 0.06 to 0.765). A total of 20 clones were selected which produced MAB 15D3.

EXAMPLE 6

Anti-MDR/hFcγRIII Bridge Assay of the Bispecific Antibody Produced By the 15D3/3G8 Hybrid Hybridomas The 20 clones selected by the anti-MDR ELISA assay of Example 5 were next screened for the production of bispecific antibody. In the following bridge assay, the supernatant from each clone was tested for its ability to cross link P-glycoprotein positive cells (K562/R7) with hFcγRIII positive cells (human PMNs). The adriamycin-selected K562/R7 cell line was obtained from Dr. B. Sikic of Stanford University, California.

A. Procedure

The effector and target cells were prepared in the following manner.

1. Preparation of Effector Cells:

PMNs and red blood cells (RBC's) were separated from heparinized human whole blood samples from normal donors by means of centrifugation through Ficoll-Hypaque. The Ficoll-Hypaque centrifugation method is generally described in *Selected Methods in Cellular Immunology*, Mishell, B. B. et al., supra). To the resulting PMN and RBC pellet was added Iscove's medium and rhodamine 123 to a final concentration of 4 μg/ml. Dextran was then added to a final concentration of 1.5%. The mixture was left standing at 37° C. for 30 minutes. Next, the supernatant (PMNs) was collected and washed with Iscove's medium, then spun at 1,000 rpm for 4 minutes. The supernatant was aspirated and the cell pellet was resuspended in 3 ml of ice cold water for 30 seconds and 1 ml of 0.6 M KCl was added. The solution was spun at 400 g for 30 minutes and the cell pellet resuspended in Iscove's medium. The PMNs were washed thrice with RPMI-1640 or Iscove's medium, and resuspended in Iscove's medium containing 10% autologous human serum at $1 \times 10^7$ cells/ml.

2. Target Cells:

The target cells, K562/R7 cells, were washed with HBSS –/–. Hydroethidine was then added to the cells to reach a final concentration of 10 μg/ml. The mixture was left standing at room temperature for 20 minutes. Next, the K562/R7 cells were washed twice with HBSS –/– and then resuspended at $2 \times 10^6$ cells/ml in Iscove's medium containing 10% autologous human serum (obtained from PMN donors).

3. Screen Assay:

50 μl of suspended PMNs was added to 50 μl of K562/R7 cells at a ratio of 4–5 effector cells to 1 target cell in a 96-well round bottom plate. In separate wells, 50 μl of the following was respectively added to the cell mixture: purified MOPC21 (final antibody concentration 10 μg/ml), 3G8 supernatant, 15D3 supernatant, and supernatant from the 20 clones. Each resulting sample was left standing 30 minutes on ice, then spun at 500 rpm for 2 minutes. The pellet was gently resuspended in 100 μl PBS and then 0.4 ml of ice cold PBS was added to this sample.

B. Result

FIG. 1 presents the result of the bridge assay. As shown in FIG. 1, very few effector cell-target cell complexes were formed in the presence of 3G8 supernatant (approximately 2%) or in the presence of 15D3 supernatant (approximately 11%). Of the 20 clones screened, two were shown to be 15D3/3G8 hybrid hybridomas. These were clones 34.5 (also known as 15D3.15) and 41.6 (also known as 15D3.18) which caused 50% and 54% of the target cells to be bound by effector cells, respectively.

EXAMPLE 7

DNA Analysis of the 15D3/3G8 Hybrid Hybridoma Clones

The following experiment showed that the DNA contents of clones 34.5 and 41.6 exceeded that of either parental hybridoma.

A. Procedure

The general procedure is described in *PNAS* (USA), 1981, 78 (12):7727. Cells from each of the clones were washed twice with PBS. The cells were then fixed with 70% cold methanol. The mixture was spun at 1,000 rpm for 4 minutes. The precipitate was resuspended in PBS containing 3 mg/ml or 15 mM of MgCl with 20 μg/ml of chromomycin A3. The mixture was left standing at room temperature for 30 minutes.

B. Result

FIG. 2 presents the DNA staining of 3G8, 15D3, and 34.5 cells. The G1 peak of 34.5 was close to the G2 peaks of 15D3, suggesting that 34.5 had lost some chromosomes but had more than the single DNA content of either parental cell.

Figure 3:
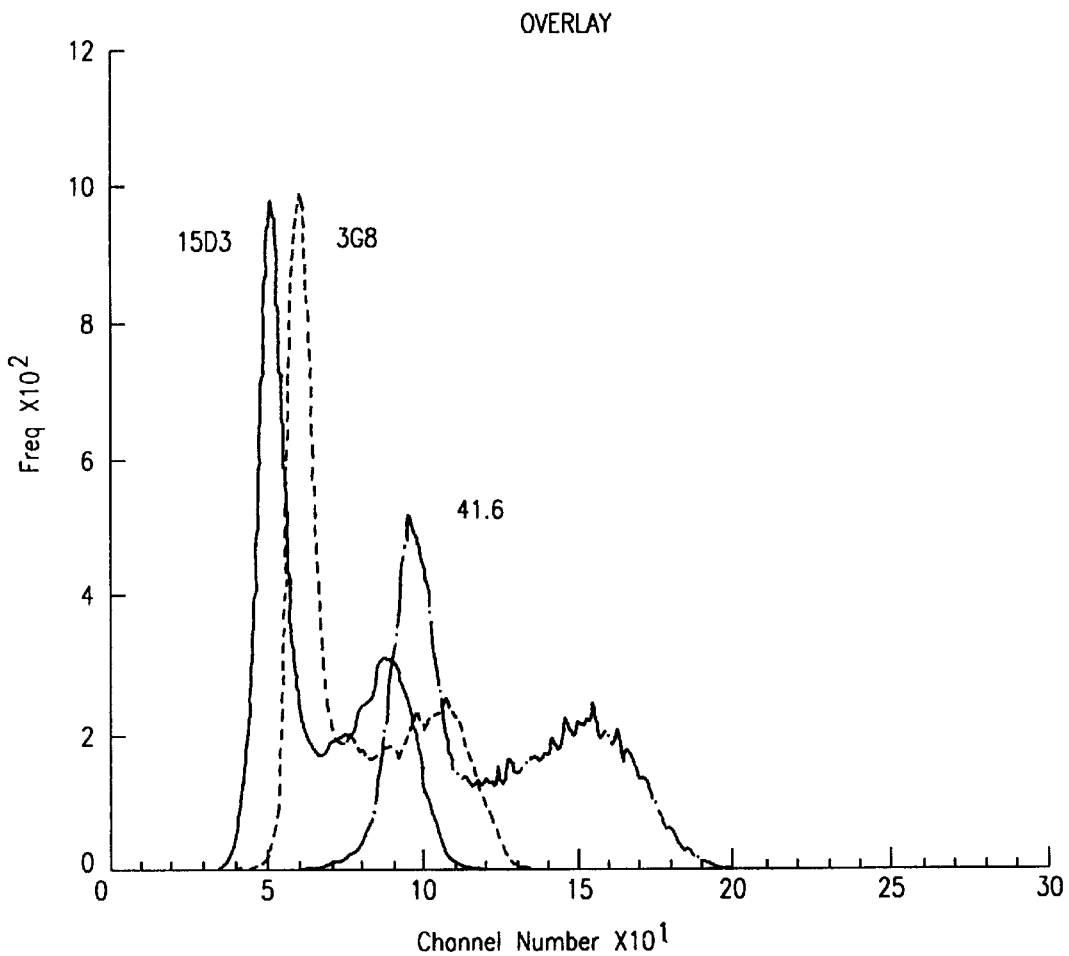
FIG. 3 presents the DNA staining of the parental hybridomas 3G8, 15D3; and hybrid hybridoma 41.6.

FIG. 3 shows the DNA staining of 3G8, 15D3 and 41.6 cells. The G1 peak of 41.6 was at the position of the G2 peaks of 15D3 and 3G8. This indicated that the DNA content of 41.6 was close to the combined amount of DNA from its parental cells.

Without wishing to be bound by the following, it is suggested that clones 34.5 and 41.6 showed less than a double DNA content when compared to their parental cells probably because these cells lost some chromosomes during proliferation. However, since they still have more than a single content of DNA, it is believed that they were actual hybrid hybridomas.

EXAMPLE 8

Collection and Purification of the Bispecific Antibodies

The following is a protocol for collecting and purifying the bispecific antibodies produced by each of the clones 41.6 and 34.5.

A. Procedure

First, the culture of each 15D3/3G8 clone was centrifuged at 500 g for 10 minutes at room temperature, and the culture supernatant collected. The supernatant was then sterile filtered using 0.2 µm pore filters. Filtrate containing the MAB was further concentrated 10-fold by ultrafiltration using Amicon YM30 membranes. The concentrate was applied to a 6×25 mm G/A garose column (Genex GammaBind™, Genex Corp., Gaitherburg, Md.) equilibrated in PBS buffer. The column was washed with 20 ml of buffer and then eluted at a flow rate of 1 ml/min with 0.5 M ammonium acetate in $H_2O$, pH 3, and fractions of 1 ml each were collected. The fractions containing the MAB were determined by $A_{280}$ and pooled. The MAB pools were then combined and dialyzed against 20 mM sodium phosphate, pH 6.2.

The entire dialysate was then injected into Mono S 5/5 cation exchange column (5 cm long column with a diameter of 5 mm) (Pharmacia/LKB, Upsula, Sweden) equilibrated in 20 mM sodium phosphate, pH 6.1. The column was washed with 5 ml of buffer and then eluted with a 40 ml gradient of 0–450 mM Nacl in 20 mM sodium phosphate, pH 6.2.

B. Result

Figure 4:
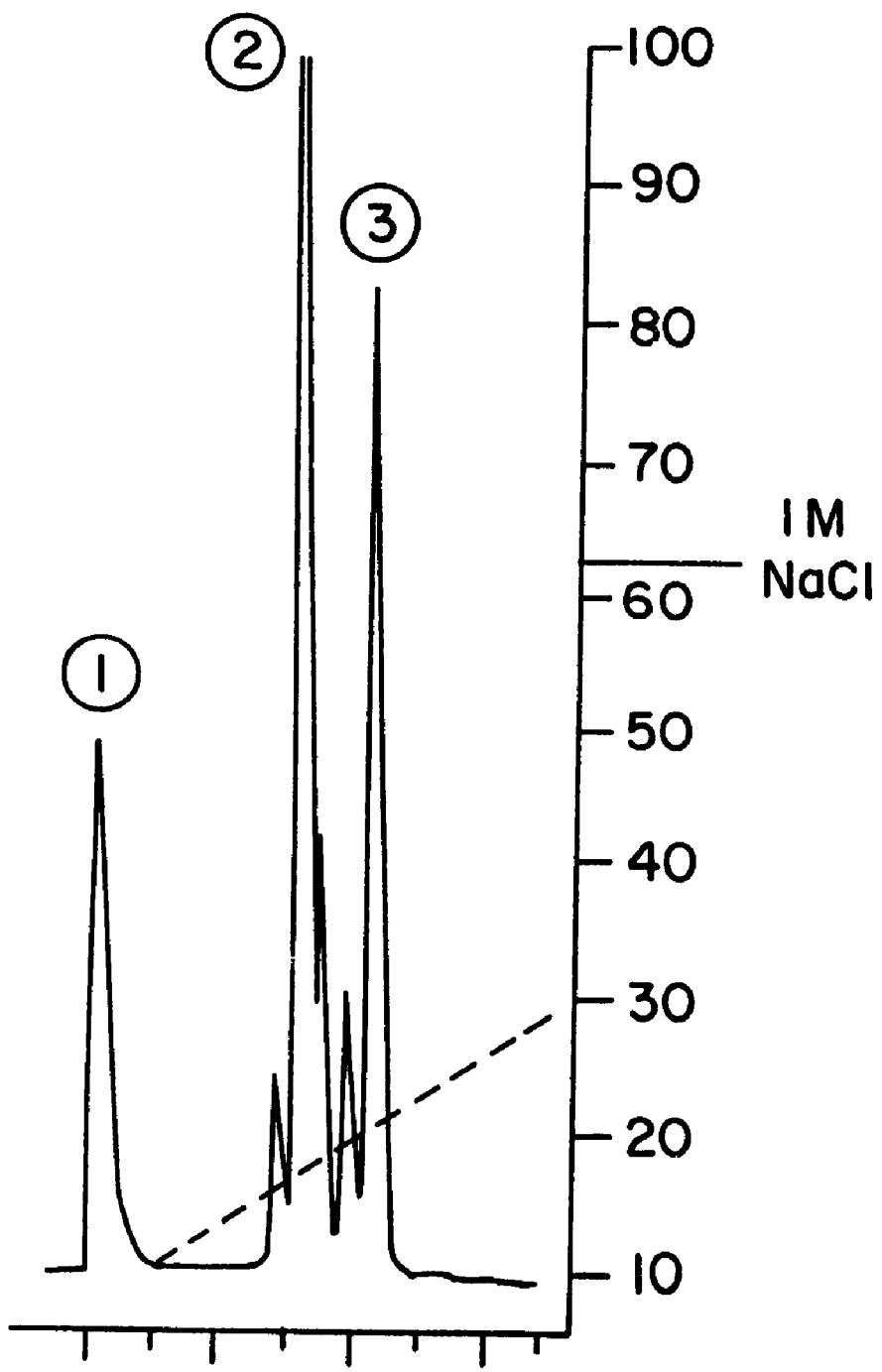
FIG. 4 presents a mono S 5/5 cation exchange column (5 cm long column with a diameter of 5 mm) elution profile for proteins produced by the hybrid hybridoma 41.6.

The eluate from the Mono 5/5 cation exchange column was analyzed and showed 3 major peaks on a UV (A280 nm) absorption traces (FIG. 4 shows the elution profile for the MAB produced by clone 41.6, which was similar to the elution profile for clone 34.5). Samples from each peak were analyzed on reducing SDS-PAGE and isoelectric focusing (IEF) gels (Pharmacia Phastgel System, Upsula, Sweden). The SDS-PAGE and IEF gels results were similar for both clones 41.6 and 34.5. On reducing SDS-PAGE, peaks 1 and 3 co-migrated with control parental MABs 3G8 and 15D3, respectively. On reducing SDS-PAGE, peak 2 material had bands that co-migrated with both parental MABs (or peaks 1 and 3). On IEF gels, peak 2 material migrated to a pI between that of the parental MABs. These results are as expected for a bispecific antibody. It was impossible to determine whether peak 2 contained heavy chains of both parental antibodies because the two heavy chains have essentially identical mobility on SDS-PAGE.

EXAMPLE 9

Assay for 15D3/3G8 Bispecific Antibody's Specific Binding to P-glycoprotein Positive Cells (K562/R7) And to hFcγRIII Positive Cells (Human PMNs)

In the following assay, both purified bispecific antibodies and their parental antibodies were used to stain P-glycoprotein positive cells (K562/R7) and hFcγRIII positive cells (human PMNs). The fluorescence intensities of the antibody stained cells were compared.

A. Procedure

The K562/R7 cells were washed twice with HBSS −/− with 1% BSA, and added into 5 ml tubes (5×10$^5$ cells per sample). To purify human PMNs, Iscove's medium was added to the PMNs pellet and RBCs pellet, which had been separated from heparinized human whole blood from a normal donor by Ficoll-Hypaque. Dextran was added to the PMN and RBC pellet to a final concentration of 1.5%, and the mixture was left standing at 37° C. for 30 minutes. The supernatant (containing PMNs) was then collected and washed with Iscove's medium. The mixture was spun 1,000 rpm for 4 minutes. The supernatant was then aspirated, and 3 ml of ice cold water was added; after 30 seconds, 1 ml of 0.6 M KCl was added. The cell suspension was spun, and the pellet resuspended in Iscove's medium. The resulting suspension containing PMNs was transferred into 5 ml tubes (1×10$^6$ PMN cells per sample. 20 µl (at 50–60 µg/ml) of purified bispecific antibodies 34.5 or 41.6, myeloma protein MOPC21, MAB 15D3 or MAB 3G8 were added to the respective tubes containing either K562/R7 cells or PMNs. Each mixture was incubated at 4° C. for 30 minutes. The cells were then thrice washed with PBS-BSA. Next, 20 µl/tube of GAM-FITC (FITC conjugated F(ab')$_2$ fragments of affinity purified and affinity adsorbed goat anti-mouse IgG, (H+L); Jackson Immuno Research Lab., Inc., West Grove, Pa.) was added. Each mixture was incubated at 4° C. for 30 minutes. The cells were then washed with PBS-BSA containing 5 µg/ml of propidium iodide.

B. Result

Figure 5:
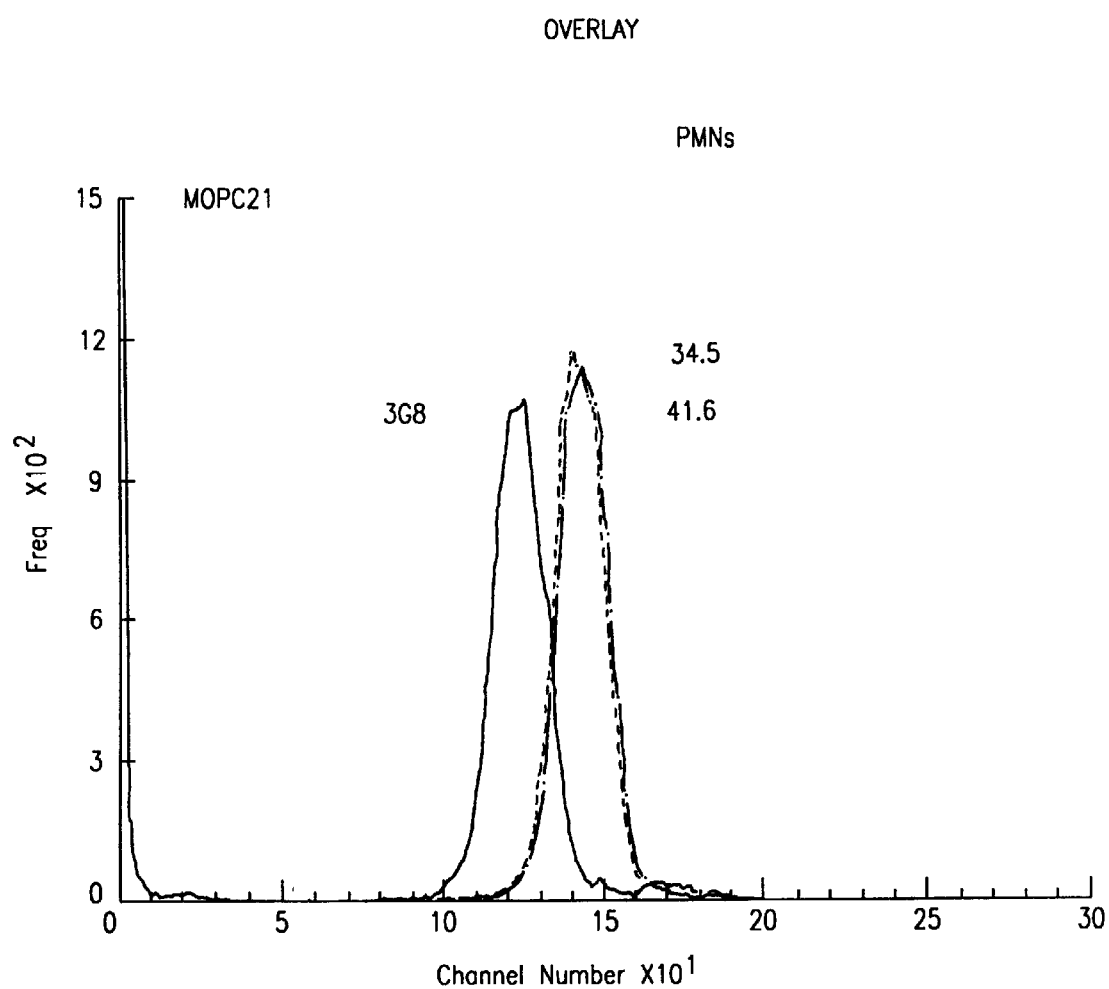
FIG. 5 presents a fluorescence histogram of stained human polymorphonuclear cells (hereinafter referred to as PMNs).
Figure 6:
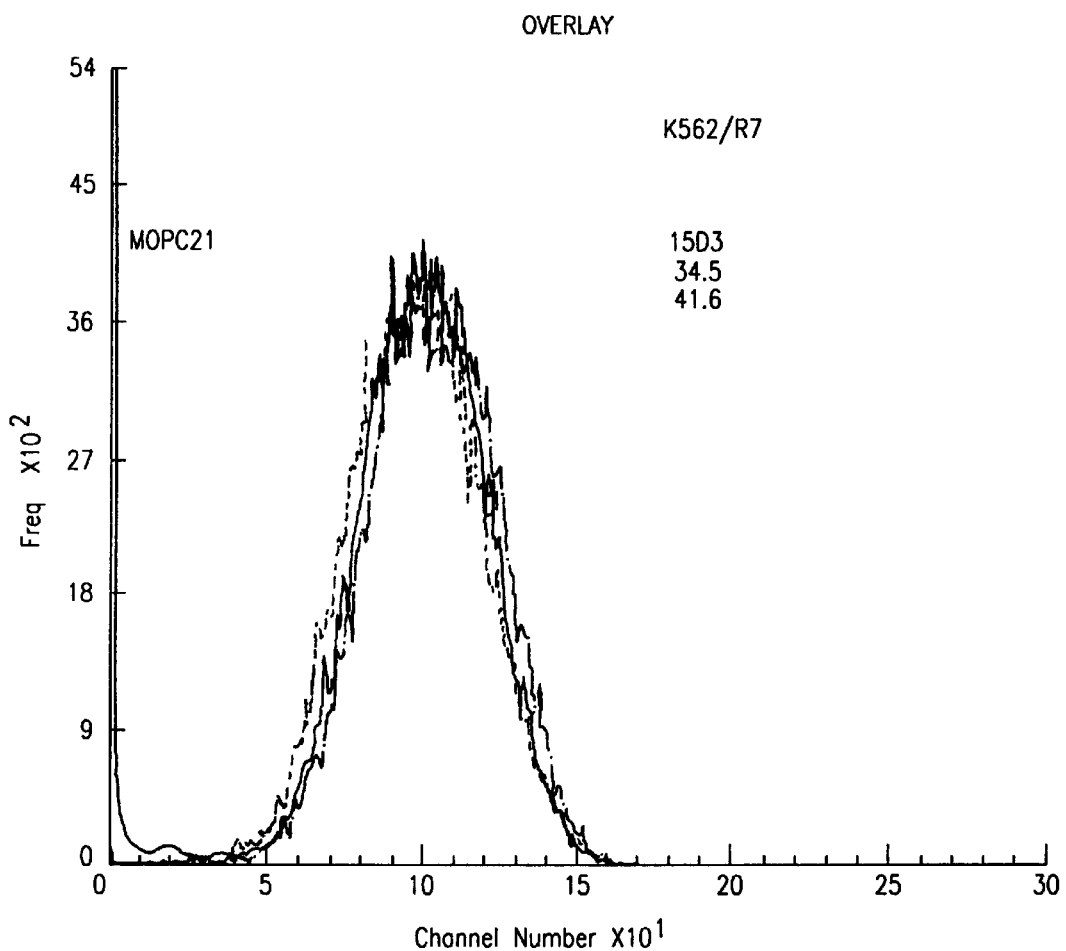
FIG. 6 presents a fluorescence histogram of stained K562/R7 cells.

The results are presented in FIGS. 5 and 6 (fluorescence histograms of stained PMNs and stained K562/R7 cells respectively).

As shown in FIG. 5, PMNs incubated with negative control MOPC21 showed a low background fluorescence. Cells stained with bispecific antibodies 34.5 and 41.6 stained equally well, and showed a peak fluorescence intensity double that of cells stained with parental antibody 3G8. This observation may reflect the fact that bispecific antibody molecules have one hFcγRIII binding site per molecule while 3G8 has two. If 3G8 binds to PMNs bivalently, a given cell should provide twice as many binding sites for a monovalent bispecific antibody.

As shown in FIG. 6, there was essentially no difference in fluorescent staining of K562/R7 cells due to parental antibody 15D3, or to purified bispecific antibodies from clones 34.5 and 41.6. Without wishing to be bound by the following, it is proposed that the similar binding of bivalent parental antibody versus monovalent bispecific antibodies in this case may have occurred because molecules of P-glycoprotein are seldom positioned so that the same antibody molecule can bind bivalently to two of them; in that case, bivalent parental antibody 15D3 would occupy as many binding sites as monovalent 15D3/3G8 bispecific antibody.

EXAMPLE 10

$^{51}$Chromium Release Assay of the Bispecific Antibodies

The three peaks eluted from Mono S 5/5 were tested in a chromium release assay, using adriamycin resistant K562/R7 target cells. The effector cells were total mononuclear cells (TMC) from two human blood donors.

In a second experiment, the purified bispecific antibodies were tested on K562 (parental), K562/R7 (adriamycin resistant), and K562/V.2 (vinblastine resistant) target cells. The latter two drug-selected lines over-express P-glycoprotein relative to the parental K562 cells.

The chromium release cytotoxicity assay is generally described in *Selected Methods in Cellular Immunology*, Mishell, B. B. et al., supra.

A. Procedure

1. Preparation of Effector Cells:

To a 50 ml tube containing 30 ml of endotoxin-free HBSS −/− was added 10 ml of heparinized blood. Next, 10 ml of separation medium Histopaque 1077 (Sigma Chemical Co., supra) was slowly pipetted directly to the bottom of the tube. The tube was then spun in an IEC DPR-6000 centrifuge (Damon Biotech, Needham Heights, Mass.) at 1250 rpm, for 25 minutes, at room temperature with the brake off. The tube was carefully removed to avoid mixing the solution. Using a Pasteur pipet the upper layer of the mixture was removed down to just above the mononuclear cell layer, which could be distinguished by its cloudy white appearance. The mononuclear cell layer was collected with a 10 ml pipet, while carefully avoiding disturbance to the red blood cell pellet. This procedure was used to process 50–60 ml of blood, depending on the number of samples to be tested. The TMC so isolated were suspended with HBSS −/− to a volume of 50 ml and centrifuged at 1250 rpm for 10 minutes at room temperature in an IEC DPR-6000 with the brake off. The supernatant was aspirated to just above the cell pellet. The pellet was resuspended using a Maxi-mix vortex and brought up to 50 ml with HBSS −/−. The resuspended cells were spun for 10 minutes at 1250 rpm, at room temperature in the IEC DPR-6000 centrifuge, without brake. The supernatant was aspirated and the pellet resuspended by using Maxi-mix vortex. Medium (consisting of Iscove's medium with 5–10% heat inactivated (56° C., 1 hour) serum from the effector cell donor, 0.03% glutamine and 50 $\mu$g/ml gentamicin) was added in an amount sufficient to achieve an effector/target ratio (E/T ratio) of about 20/1 in a total volume of 0.2 ml/well. This amounted to approximately $2\times10^6$ effector cells/ml.

2. Preparation of the Target Cells:

After the effector cells had been isolated and prepared, or simultaneously therewith, the target cells were prepared. In this experiment, to insure a highly viable cell population, the target cells were labelled with chromium while the TMCs were being prepared. The target cells were grown to near confluence (or late log phase for suspension cultures) in standard laboratory T150 cm$^2$ flasks, and fed with fresh medium the day before the experiment. If the target cells were non-adherent, the cells were washed once with 50 ml of HBSS −/−, spun at 1000 rpm and resuspended in 1.0 ml of growth medium. If adherent target cells were used, the adherent cells were washed twice with 10 ml of HBSS −/− and the cells removed from the flask by washing the monolayer with 10 ml of sterile 1/5,000 versene, incubating the flask at 37° C., 5% $CO_2$ for 3 to 5 minutes, and dislodging the cells by banging the flask against a solid surface. Next, 10 ml of growth medium was added to suspend the cells. The growth medium consisted of: endotoxin free Iscove's medium (IMDM) (JR Scientific, Woodland, Calif.) and 5–10% autologous human serum. The cell suspension was transferred to a 50 ml siliconized polypropylene tube. The volume was increased to 50 ml with HBSS −/−. A cell count was taken to determine viability and cell number. The cells were spun for 10 minutes at 1000 rpm at room temperature. The supernatant was aspirated off and the pellet resuspended with 1 ml of growth medium by gently pipetting the suspension up and down. 122 $\mu$Ci of $^{51}$chromium ($^{51}$Cr) were added per target cell line tested (approximately $1–3\times10^7$ cells for either adherent or suspension target cells).

The mixture was incubated for 45 minutes at 37° C. The tube was swirled every 10 minutes to maintain the cells in semi-suspension. Five ml of HBSS −/− was then added to $^{51}$Cr target cells and the tube was gently swirled to mix the components and then spun for 10 minutes at 1000 rpm at room temperature. The supernatant was removed with a pasteur pipet. The cell pellet was resuspended with 2 ml of HBSS −/− by pipetting action. HBSS −/− was added to bring the total volume of the tube to 50 ml. The mixture was incubated for 30 minutes at 37° C. The tube was spun at 1000 rpm for 10 minutes. The supernatant was aspirated off. To remove residual chromium, the cells were washed again with 50 ml of HBSS −/−. The tube was spun at 1000 rpm for 10 minutes. The supernatant was aspirated and the pellet was resuspended in 2 ml of growth medium. The cell count was taken and the cells diluted to a final density of $2\times10^4$ cells/well in 0.1 ml or $2\times10^5$ cells/ml.

3. Mixing Target and Effector Cells:

0.1 ml of labelled target cells/well was added to a 96-well polystyrene V-bottom microtiter plate containing 0.1 ml/well of growth medium alone or containing hybrid hybridoma supernatant, purified antibodies, or control (medium alone, without antibody); final volume was approximately 0.2 ml/well. The plates were incubated at 37° C., 5% $CO_2$ for 1 hour. The plates were spun in a Beckman J6-B centrifuge at 1000 rpm for 15 minutes. The supernatant was aspirated using a 6-prong aspirator. 0.2 ml of effector cells/well was added to target cells or 0.2 ml of growth medium (for spontaneous chromium release) or 0.2 ml of 1.0% Nonidet P-40 (NP-40, Sigma Chemical Co., supra) in distilled water (for maximum release of the chromium from the labelled target cells). The plates were incubated at 37° C., 5% $CO_2$ for 3 hours. Next, the plates were spun in a Beckman J6-B at 1000 rpm for 15 minutes at room temperature to pellet the cell mixture. With a 12-channel pipet, 0.1 ml aliquots of the supernatant were transferred into micro-test tubes. The samples were counted in a gamma counter using the chromium program to determine the percent lysis and degree of cytotoxicity.

B. Result

Figure 7:
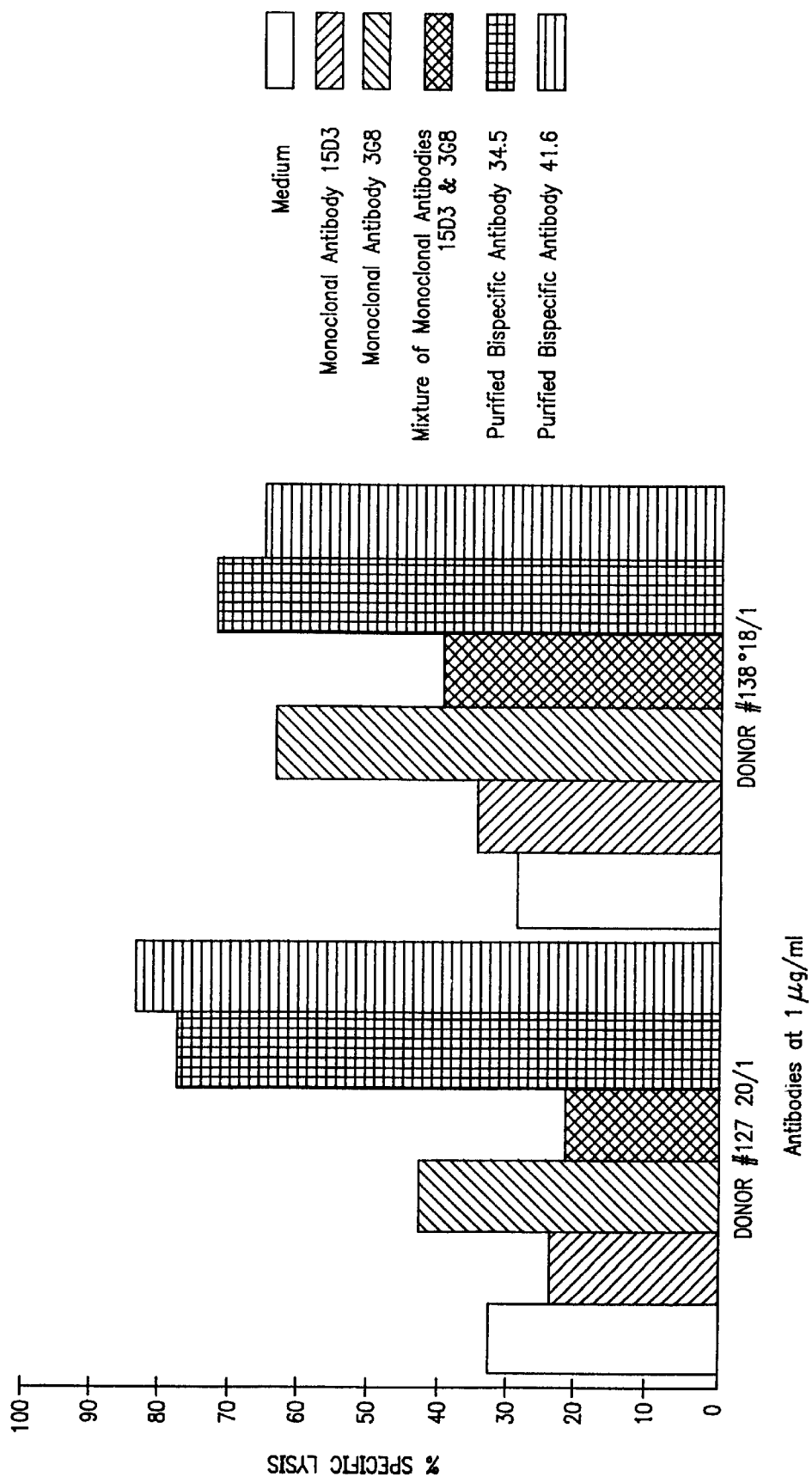
FIG. 7 presents the $^{51}$chromium release assay (hereinafter referred to as $^{51}$Cr release assay) of 15D3/3G8 bispecific antibodies, using TMC (total mononuclear cells) in media containing 8–10% heat inactivated autologous human serum and K562/R7 target cells.

The following experiments tested the bispecific antibodies produced by hybrid hybridomas 34.5 and 41.6 grown in FBS-containing and serum free media. The FBS-containing medium consisted of Iscove's IMDM and 10% heat-inactivated FBS and OPI (0.15 mg/ml cis-oxalacetic acid, 0.05 mg/ml pyruvic acid, and 0.2 units/ml insulin). The composition of the serum free medium is disclosed in Table 1, column 3 of patent application, "Cell Culture Medium for Enhanced Cell Growth, Culture Longevity and Product Expression," to Howarth, W. et al., published under the Patent Cooperation Treaty, International Publication No. WO 90/03430, with the international publication date of Apr. 5, 1990. The antibodies were purified from the middle peaks of the Mono S columns (as in Example 9). As shown in FIG. 7, the chromium release assay showed that bispecific antibodies 34.5 and 41.6 purified from serum free supernatants mediated lysis of the drug resistant K562/R7 cells at about twice background (the signal observed without antibody). The results were similar for effector cells from both human donors. Bispecific antibodies 34.5 and 41.6 purified from serum containing medium showed similar results (results not shown in Figures). On the other hand, the antibodies produced by the parental hybridomas 15D3 and 3G8 (but not antibody 3G8 in the case of Donor #138) did not mediate significant lysis, nor did the mixture containing both antibodies 15D3 and 3G8. Without wishing to be bound by any theory, it is postulated that the high level of lysis mediated by antibody 3G8 in the case of Donor #138 probably reflected non-specific lysis.

Figure 8:
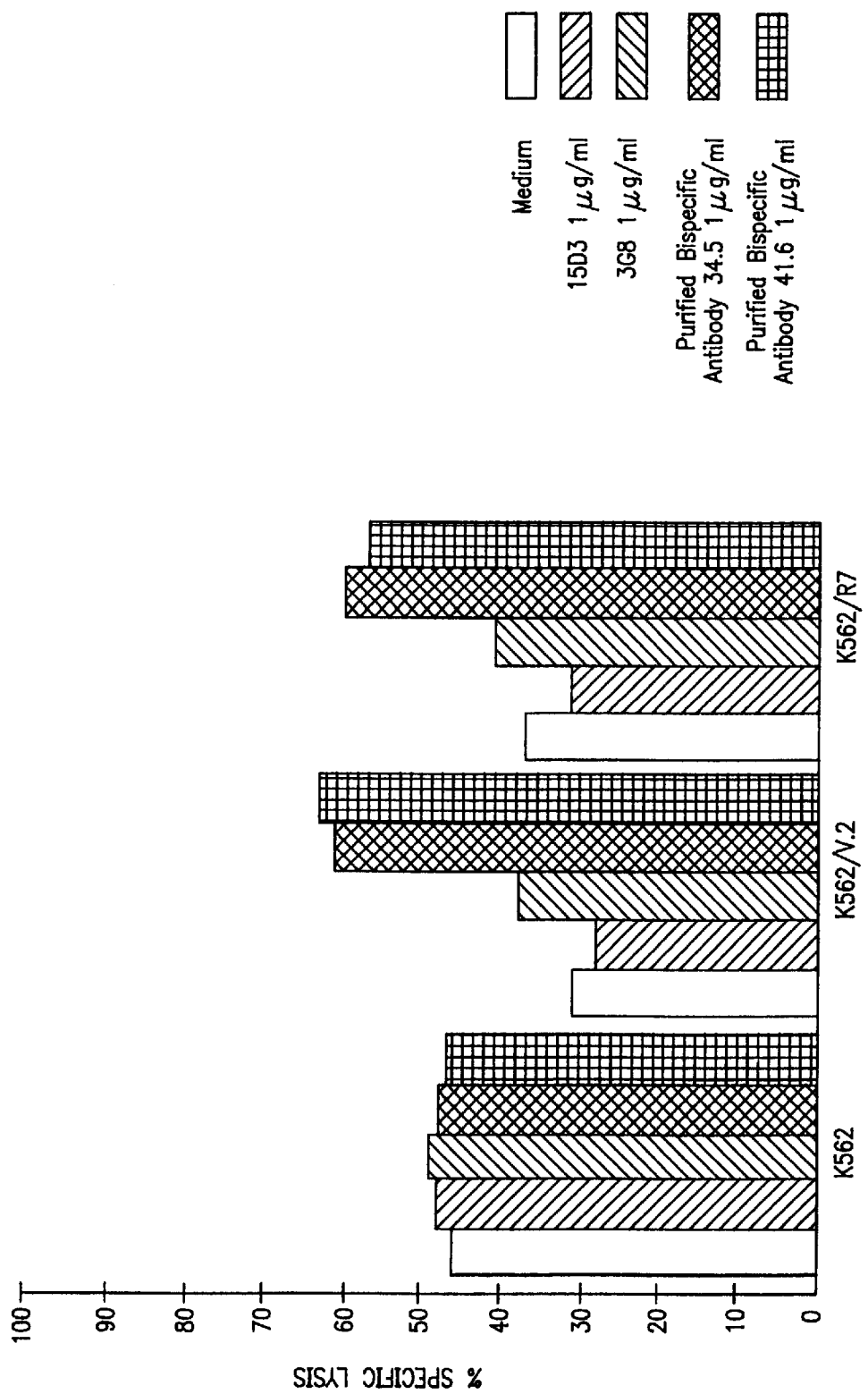
FIG. 8 presents a $^{51}$Cr release assay using 15D3/3G8 bispecific antibodies with TMC from a donor at an effector to target ratio of 12/1 in a medium containing 10% heat inactivated autologous human serum.
Figure 9:
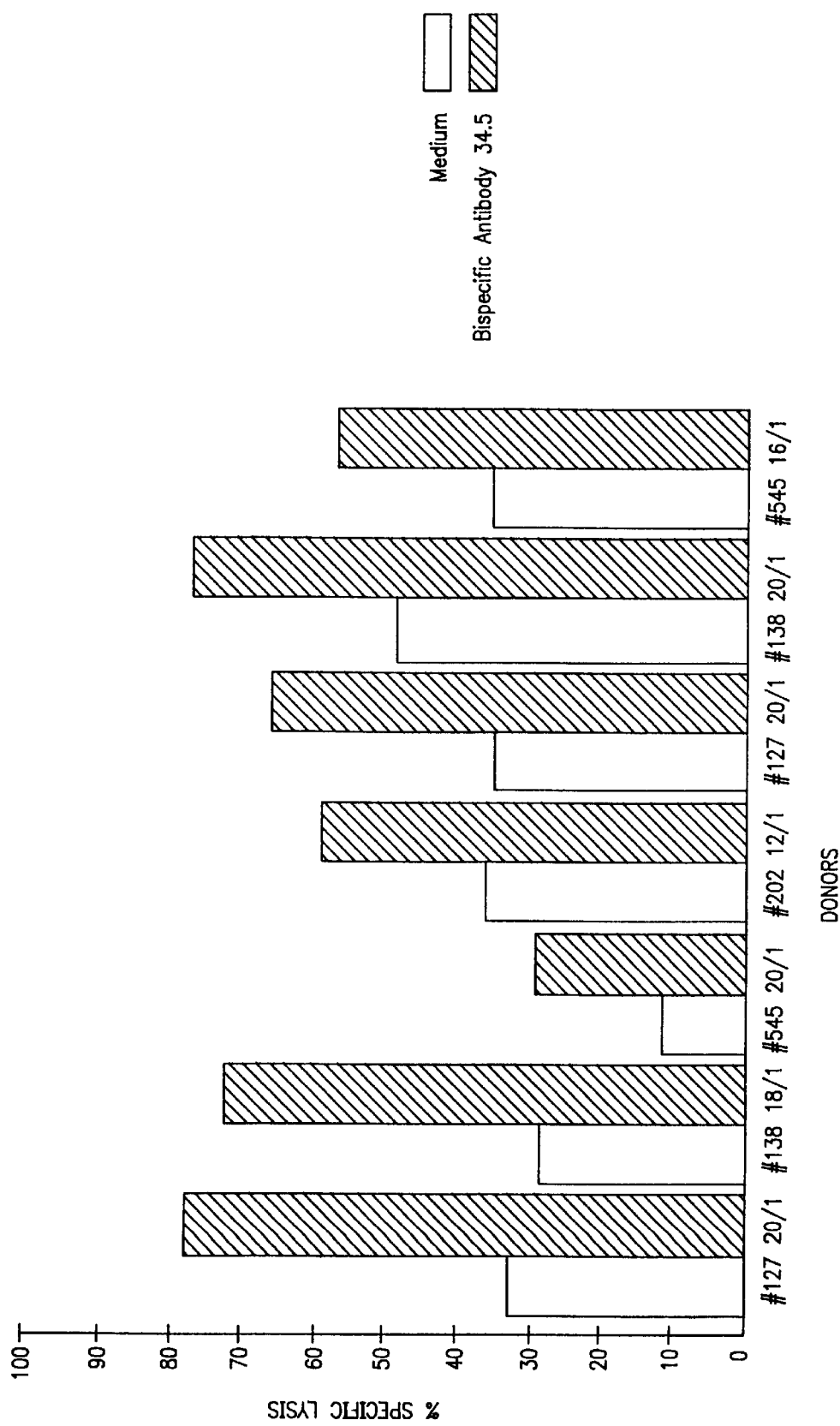
FIG. 9 presents a $^{51}$Cr release assay using 1 μg/ml of bispecific antibody 34.5 on K562/R7 target cells, and TMC from various human donors.
Figure 10:
FIG. 10 presents a $^{51}$Cr release assay using bispecific antibody 34.5 on various target cells, using TMC from donor #138.
Figure 11:
FIG. 11 presents a $^{51}$Cr release assay of bispecific antibody 34.5 on various cell lines using TMC from donor #545.

The result of the second experiment (FIG. 8) showed that the background lysis levels of the two resistant cell lines, K562/R7 and K562/V.2, were lower than that of the parental NK sensitive K562 cells. The two purified bispecific antibodies, 34.5 and 41.6, did not mediate any specific lysis of drug resistant K562 cells. However, the bispecific antibodies mediated the specific lysis of drug resistant K562/R7 and K562/V.2 cells. Bispecific antibody 34.5 mediated specific lysis of K562/V.2 at 62% (which was 94% above the background lysis of 32%). FIG. 9 shows the results of tests on bispecific antibody 34.5 using effector cells from 7 donors and K562/R7 target cells. The bispecific antibody 34.5 had also been tested against and found to lyse other MDR cell lines, e.g. MES-DX5, KB-A1, and KB-V1. However, bispecific antibody 34.5 did not mediate the lysis of non-MDR cell line KB-3-1 or a non-MDR, human breast adenocarcinoma cell line SKBr3. (See FIGS. 10 and 11)

The mono S chromatography of proteins produced by subclone 1A7 (a stable subclone of 34.5), was similarly analyzed (Example 11 below presents 1A7). The mono S chromatography of proteins produced by subclone 1A7 showed three peaks similar to those observed in Example 9. The protein collected from all 3 peaks eluted from the mono S chromatography of 1A7 were tested in the chromium assay. Also tested was bispecific antibody 34.5. The target cell lines were K562 and K562/V.2. The K562/V.2 cell lines were first grown for 48 hours in 0.1 μg/ml vinblastine containing medium, or in drug-free medium, respectively.

Figure 12:
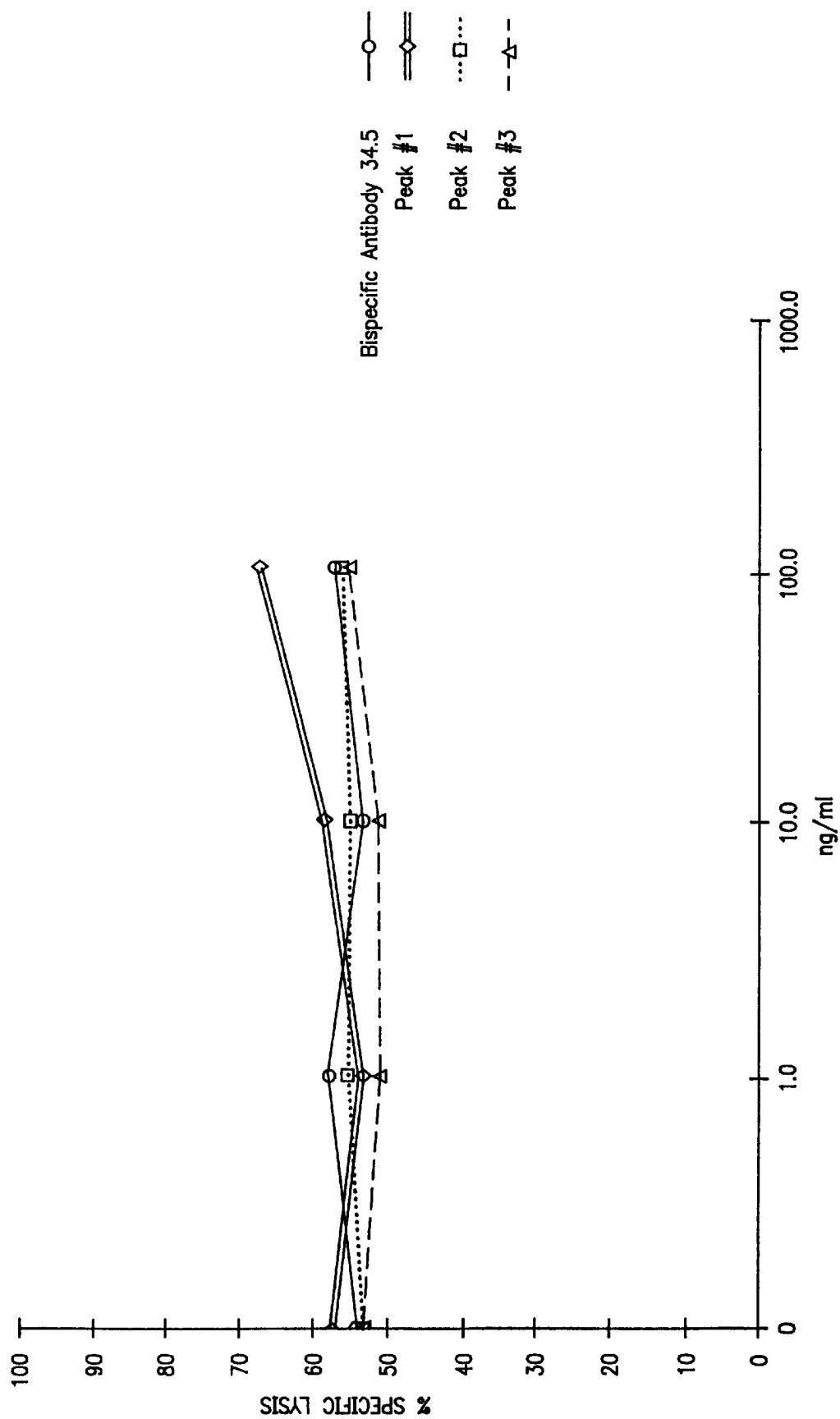
FIG. 12 presents the titration of 3 peaks from the purification of bispecific antibody 1A7 using a $^{51}$Cr release assay with K562 cell line and autologous human serum.
Figure 13:
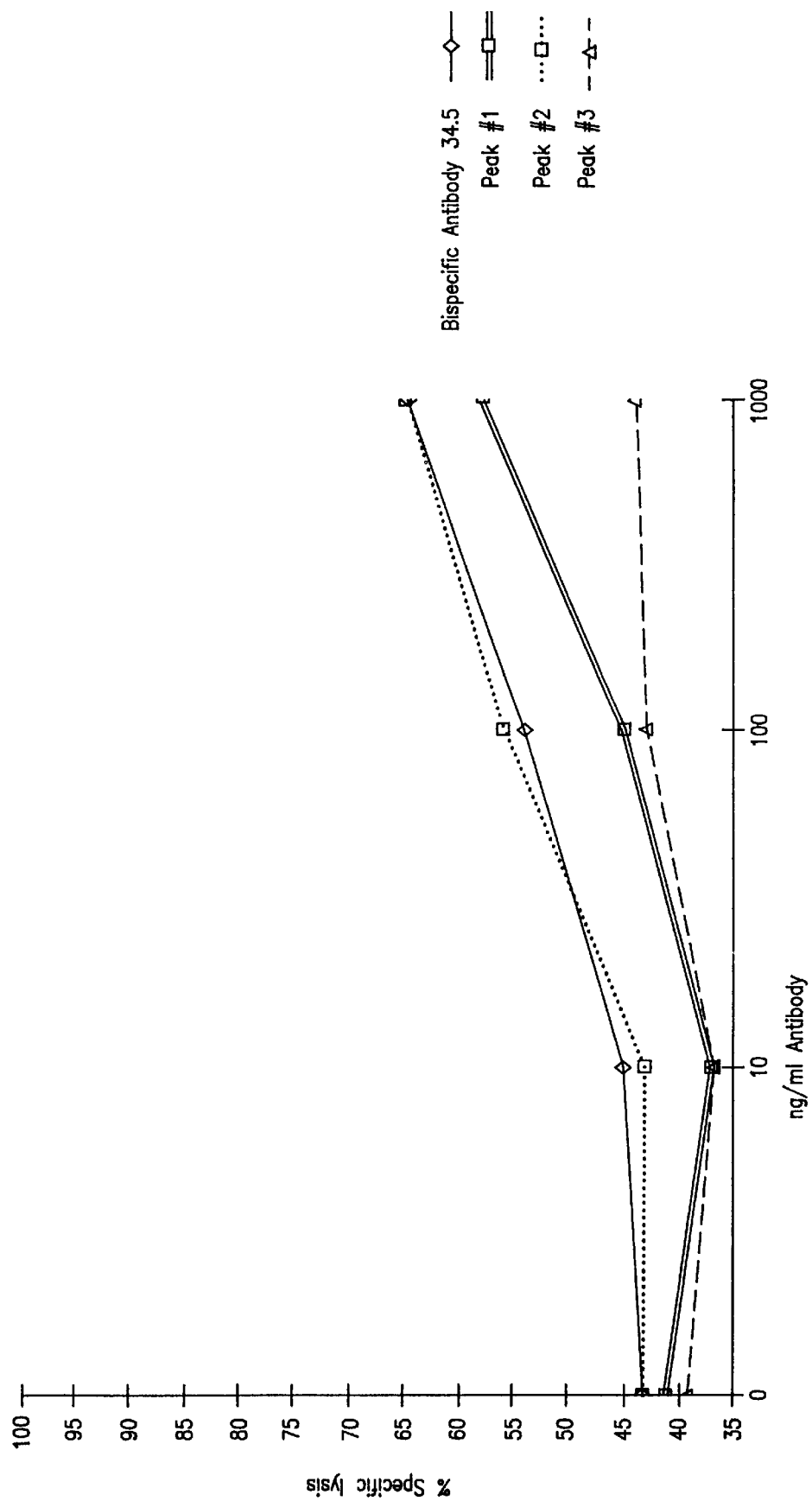
FIG. 13 presents the titration of 3 peaks from the purification of bispecific antibody 1A7 in a $^{51}$Cr release assay using K562/V.2 cell line (grown in drug-free medium) and autologous human serum.
Figure 14:
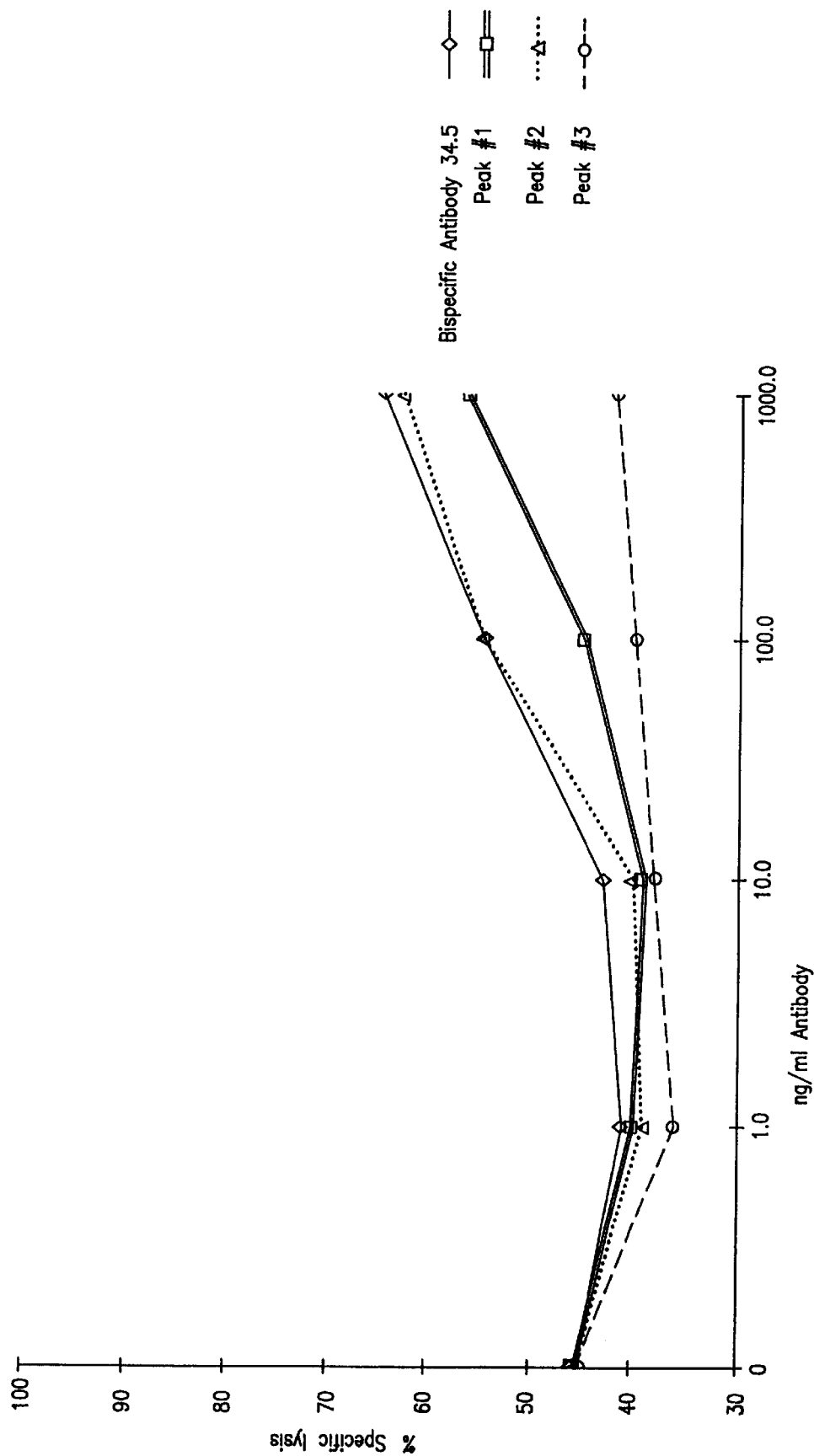
FIG. 14 presents the titration of 3 peaks from the purification of bispecific antibody 1A7 in a $^{51}$Cr release assay using K562/V.2 (grown in a medium containing 0.2 μg/ml vinblastine).

Chromium release assay results indicated that peak 2 contained bispecific antibody 1A7 and that the activity of this purified material is comparable to that of the purified bispecific antibody 34.5 when tested against the MDR target cell line K562/V. 2 (FIGS. 13 and 14). Significantly, the lysis results for the two K562/V.2 cell lines, one grown in drug free medium, and the other grown in drug containing medium, were similar (FIGS. 13 and 14). The protein collected from all 3 peaks eluted from mono S chromatography of 1A7 and 34.5 showed that the lysis levels of the non-MDR cell line K562 were similar to the background lysis using the medium alone (FIG. 12). Without wishing to be bound by the following postulation, it is postulated that the high levels of lysis resulted from the NK sensitive nature of the K562 cell line.

To further assess the activity of the bispecific antibody from subclone 1A7, it was tested against a panel of MDR cell lines and one non-MDR cell line. The antibody was titrated in 10-fold steps from 1000 ng/ml down to 1 ng/ml. The positive control was purified bispecific antibody 34.5. The target cell lines were: K562/V.2, MES-DX5, KB-A1, KB-V1 and KB-3-1. The growth conditions of the cells were as shown in Table 1, above.

Figure 15:
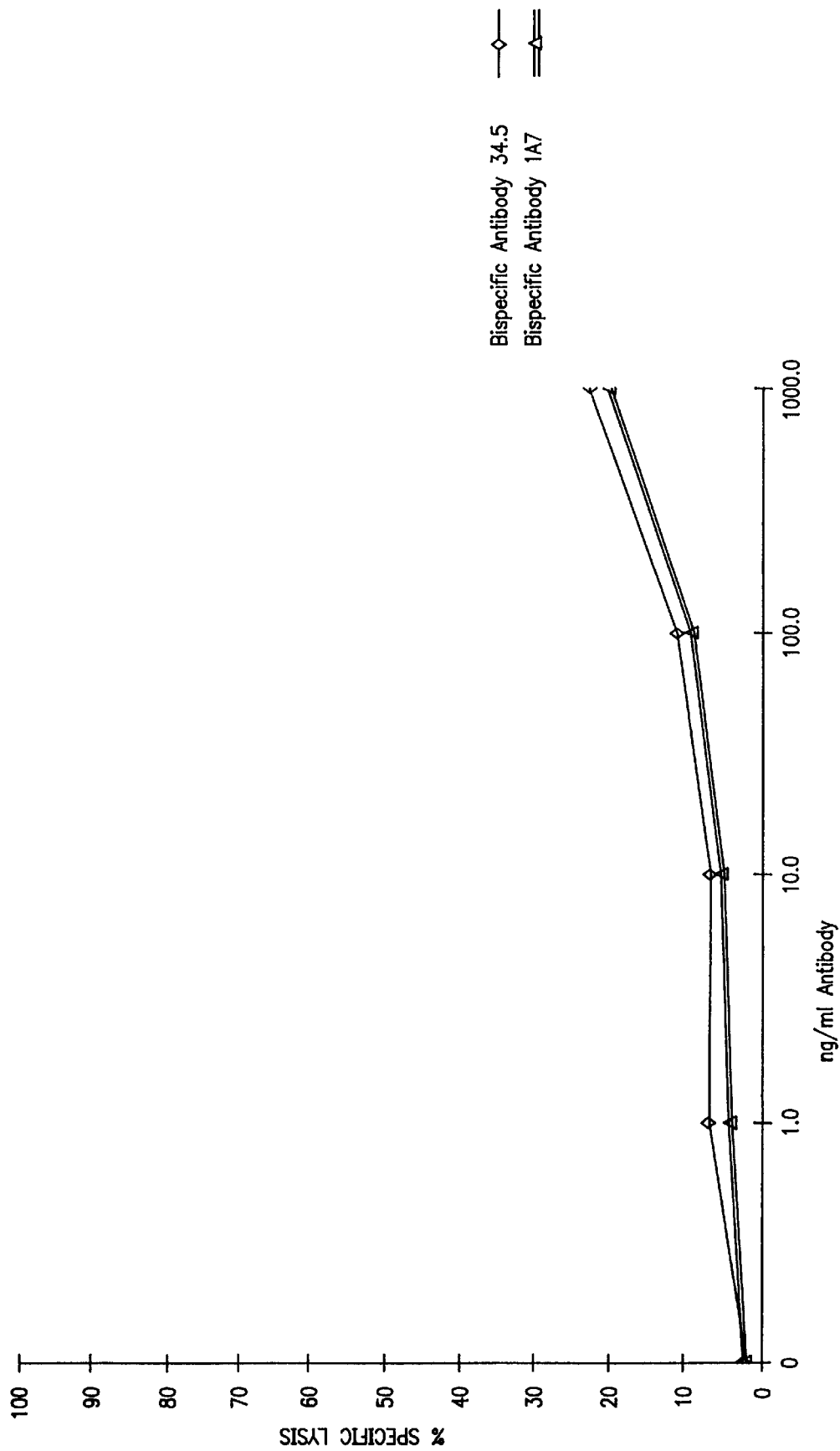
FIG. 15 presents the $^{51}$Cr release assay titration of bispecific antibody 1A7 in medium containing autologous human serum using KB-A1.
Figure 16:
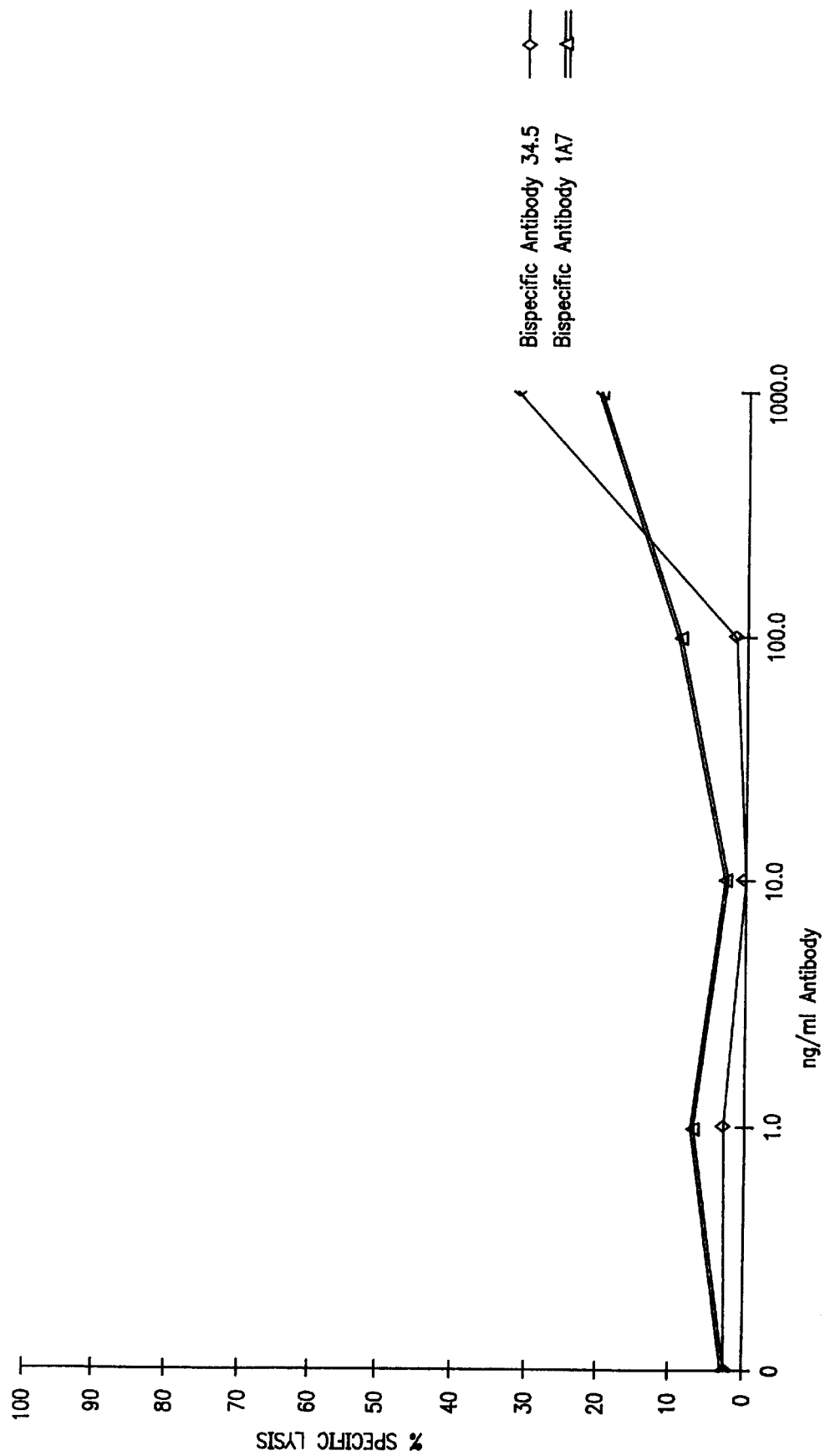
FIG. 16 presents the $^{51}$Cr release assay titration of bispecific antibody 1A7 using medium containing autologous human serum with MDR cell line KB-V1.
Figure 17:
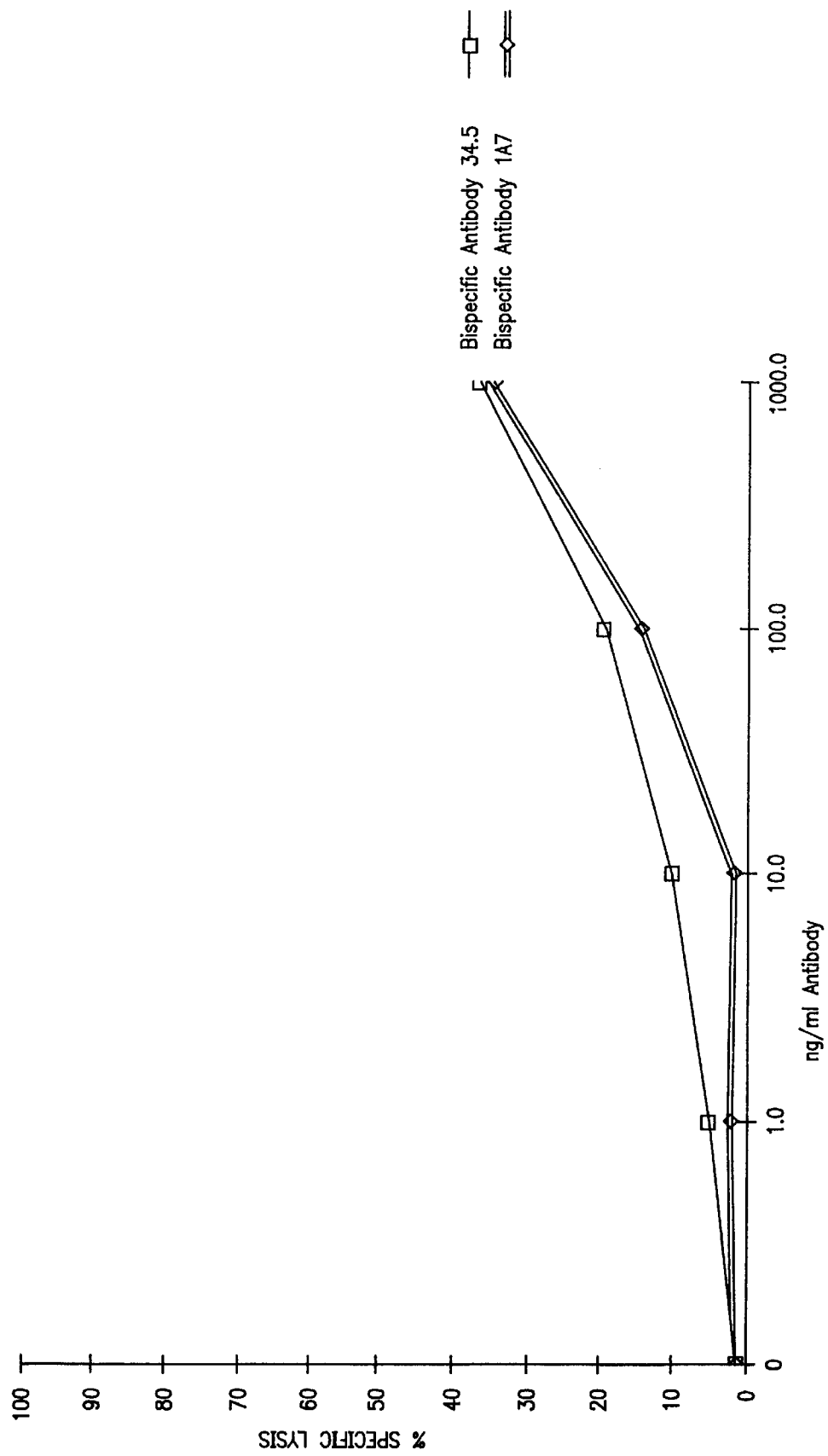
FIG. 17 presents the $^{51}$Cr release assay titration of bispecific antibody 1A7 in medium containing autologous human serum using MDR cell line MES-DX5.
Figure 18:
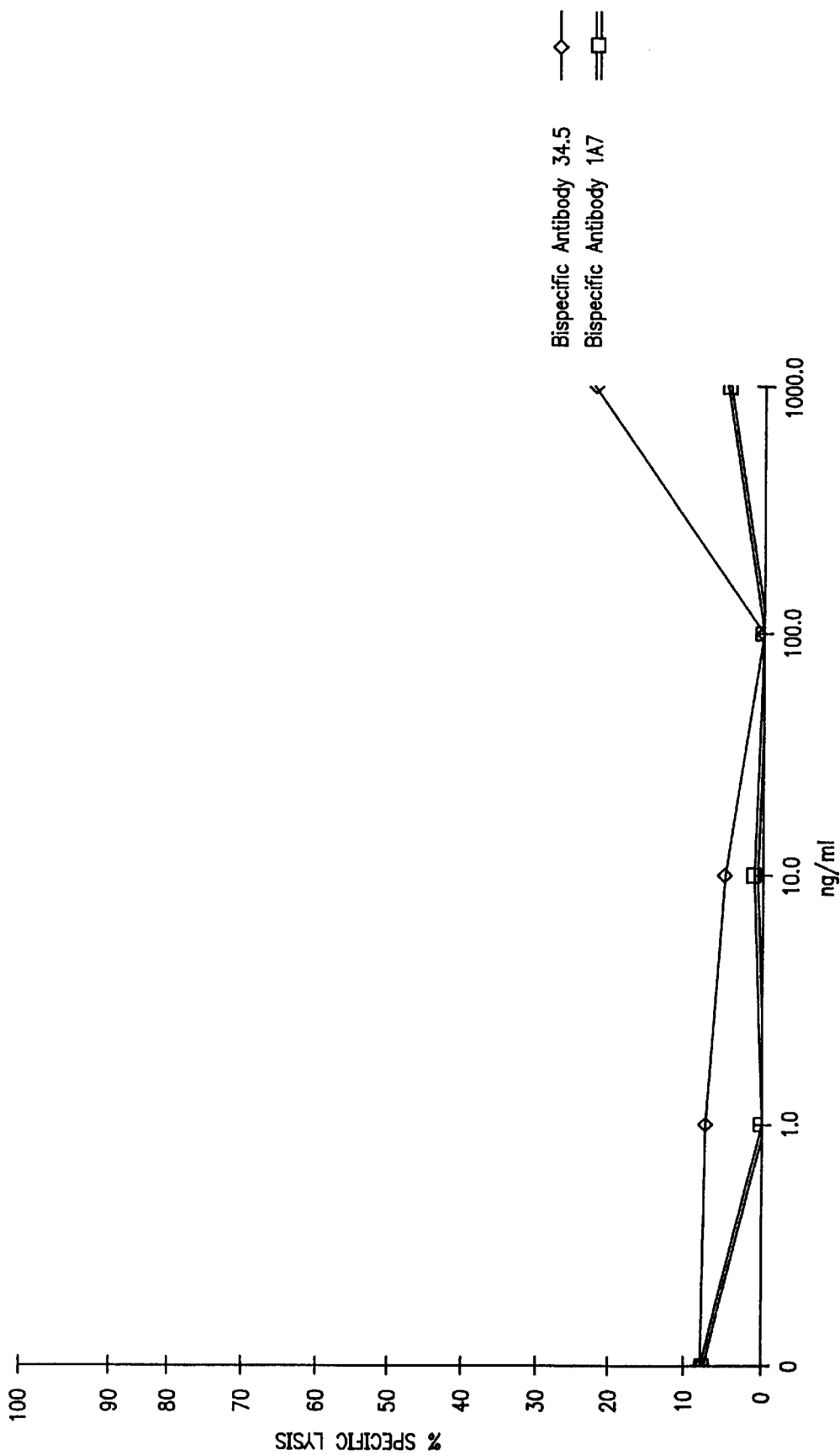
FIG. 18 presents the $^{51}$Cr release assay titration of bispecific antibody 1A7 in medium containing autologous human serum using sensitive cell line KB-3-1.

The results (FIGS. 15 to 17) showed that bispecific antibodies 1A7 and 34.5 mediated the specific lysis of the MDR cell lines at levels well above background at a concentration of 1000 ng/ml. The non-resistant line, KB-3-1, was not lysed much above background levels when tested with bispecific antibody 1A7 (FIG. 18).

EXAMPLE 11

Obtaining Stable Clones of the Quadromas by Subcloning

A. Procedure

To insure stable antibody producing clones, the clones 34.5 and 41.6 were subcloned in 75% (Iscove's medium containing 15% heat incubated FBS and 2 mM glutamine) mixed with 25% conditioned medium filtered off (0.2 micron filter, Nalge Co., Rochester, N.Y.) growing cultures of SP2/0 myeloma cells. The supernatants from growing wells were tested in chromium release assays using various MDR cell lines. Subcloning of each line was pursued until 90% or more of the wells tested were positive in mediating the lysis of MDR cell line K562/R7. The clone producing the most antibody in each round of subcloning was submitted for mycoplasma testing and use for the next step of subcloning. The following presents the procedures for mycoplasma test, and subcloning for the clones 34.5 and 41.6, respectively.

1. Mycoplasma Testing:

$1\times10^4$ cells from each hybrid hybridoma line were added in duplicate to a tissue culture chamber slide (2 chambers/slide) seeded with $1\times10^4$ cells/chamber of Vero cells. The positive and negative controls were BHK and Vero cell lines respectively. The cells were incubated for 3 days, at the end of which the supernatant was aspirated. The cells were washed with 1 ml of PBS. 0.5 ml/slide of fixative consisting of acetic acid and methanol (at the ratio of 1:3) was added. After 3 to 5 minutes, the supernatant was aspirated. Next, 1 ml/slide of Hoechst Dye (CALBIOCHEM, La Jolla, Calif.) diluted with PBS at the ratio of 1:100 was added to the cells. After 25–30 minutes, the supernatant was aspirated. The disposable culture chambers were removed and each slide was rinsed with water for 5 minutes. The slide was allowed to air dry and was then examined under a fluorescence microscope.

2. Subcloning of 34.5:

Clones from the 34.5 line were seeded at 1 cell/well. Out of the 192 seeded wells, 6 wells produced viable clones which were tested in the chromium release assay described in Example 10 above. The supernatants from 5 of the 6 clones mediated the lysis of K562/R7. One of the clones which caused lysis, 2E5, was further subcloned at 0.5 and 1 cell/well. 40/49 (i.e. 82%) of the wells tested from this cloning mediated the lysis of K562/R7. Ten of the positive clones selected were retested using K562R7 and K562/V.2 as targets, and all ten clones mediated lysis of both cell lines. Clone 4G12 was selected from this group and subcloned at 0.5 cell/well. 20/22 (i.e. 91%) of the 4G12 subclones mediated the lysis of K562/R7. Clone 1A7 was selected from this set and it also mediated the lysis of MES-DX5 and K562/V.2. clone 1A7 has been deposited with the American Type Culture Collection on Jul. 10, 1990 under the deposit number ATCC HB10501. Subclones 2E5, 4G12, and 1A7 all tested negative for mycoplasma.

3. Subcloning of 4.16:

The 41.6 cell line was subcloned at 1 cell/well, which yielded 5/192 growing wells. The clones from 3 of the 5 growing wells mediated the lysis of K562/R7. Clone 1A3 was selected from the clones which mediated lysis, and subcloned at 0.5 cell/well. 22/24 (96%) of the clones tested from these subclones mediated the lysis of K562/R7. Clone 1B7 was selected from the set and it also mediated the lysis of MES-DX5 and K562/V.2. Clone 1B7 has been deposited with the American Type Culture Collection on Jul. 10, 1990 under the deposit number ATCC HB10500. Subclones 1A3 and 1B7 both tested negative for mycoplasma.

EXAMPLE 12

Medical Treatments Using 15D3/3G8 Bispecific Antibody

The 15D3/3G8 bispecific antibody can be used for treatment of tumors which exhibits the MDR phenotype, more particular those which over-express P-glycoprotein. The bispecific antibody can be administered in a physiologically acceptable carrier. The bispecific antibody can also be administered as an armed effector cell composition as described previously under "6. Composition of Cytotoxic Cells Armed with Bispecific Antibodies". Further, as described previously, in the case of the armed effector cell composition, the effector cells can be activated with one or more activating factor(s) before they are armed with the bispecific antibodies. Alternatively, the activating factor(s) can be administered separate from, or as part of the bispecific antibody composition or armed effector cell composition. The activating factor(s) can also be administered to the patient before or during the treatments.

The amounts of bispecific antibodies, effector cells, armed effector cell composition, or activating factor(s) administered will vary depending on the condition of the tumor and patient. In general, the amount will be sufficient to obtain localization at the target cell (tumor cell over-expressing P-glycoprotein) and to effect killing of the target cell by lysis through the cross-linking of the target cell with effector cells expressing hFcγRIII. The routes of administration can also vary. For example, depending on the localization of the tumor, the bispecific antibody, armed effector cell composition and activating factor(s) can be administered intravenously, or in the case of ovarian carcinoma, directly into the peritoneal cavity.

Each of the above treatment regimens can be performed in conjunction with other techniques for the removal of the targeted cells, for example, surgery, chemotherapy or radiotherapy. Further, combination immunotherapy may be used to direct two distinct effector or cytotoxic populations toward tumor cell rejection. For example, other anti-tumor bispecific antibodies may be concurrently used. Protocols based on these concepts may be especially effective in removing residual tumor cells in patients induced into remission by chemotherapy and irradiation.

Deposition of Cultures

The hybrid hybridomas clones 1A7 and 1B7, used in the above examples to illustrate the method of the present invention were deposited in and accepted by the American Type Culture Collection (ATCC), 10801 University Boulevard, Manassas, Va. 20110-2209, USA, on Jul. 10, 1990, under the terms of the Budapest Treaty.

Availability of the deposited cell lines is not to be construed as a license to practice the invention in contravention of the rights granted under the authority of any government in accordance with its patent laws.

Also, the present invention is not to be considered limited in scope by the deposited hybrid hybridomas, since they are intended only to be illustrative of particular aspects of the invention. Any animal cell line (including any hybrid hybridoma or trioma), which can be used for the production of the bispecific antibodies according to the methods described in this patent application is considered within the scope of this invention. Further, various modifications of the invention in addition to those shown and described herein apparent to those skilled in the art from the preceding description are considered to fall within the scope of the appended claims.

The present invention has been described with reference to specific embodiments. However, this application is intended to cover those changes and substitutions which may be made by those skilled in the art without departing from the spirit and the scope of the appended claims.

We claim:

1. A method for treating a disease state comprising the steps of:
   (a) administering to a patient in need of such treatment a therapeutically effective amount of a bispecific antibody obtained from a hybrid hybridoma on deposit with the American Type Culture Collection, with Accession No. HB10500 or HB10501, wherein said antibody is capable of binding to both (i) Fc receptors of cytotoxic cells, and (ii) tumor cells exhibiting multi-drug resistance phenotype, wherein the tumor cells over-express P-glycoproteins as compared to normal cells; and
   (b) monitoring the progress of the disease state and, if desired, repeating the administration.

2. The method of claim 1, wherein the Fc receptors comprise human FcγRIIIs.

3. The method of claim 2, further comprising the step of administering to the patient an effective amount of one or more of the following: IL-2 and M-CSF.

4. The method of claim 1, wherein the bispecific antibody is obtained from the hybrid hybridoma on deposit with the American Type Culture Collection, with Accession No. HB10500.

5. The method of claim 1, wherein the bispecific antibody is obtained from the hybrid hybridoma on deposit with the American Type Culture Collection, with Accession No. HB10501.

6. A method for treating a disease state comprising the steps of:
   (a) administering to a patient in need of such treatment a therapeutically effective amount of a plurality of bispecific antibodies obtained from a hybrid hybridomas on deposit with the American Type Culture Collection, with Accession Nos. HB10500 or HB10501, wherein said antibodies are capable of binding to both (i) Fc receptors of cytotoxic cells, and (ii) tumor cells exhibiting multi-drug resistance phenotype, wherein the tumor cells over-express P-glycoproteins as compared to normal cells; and
   (b) monitoring the progress of the disease state and, if desired, repeating the administration.

7. The method of claim 6, wherein the Fc receptors comprise human FcγRIIIs.

8. The method of claim 6 further comprising the step of administering to the patient an effective amount of one or more of the following: IL-2 and M-CSF.

9. The method of claim 6, wherein one of said plurality of bispecific antibodies is obtained from the hybrid hybridoma on deposit with the American Type Culture Collection, with Accession No. HB10500.

10. The method of claim 6, wherein one of said plurality of bispecific antibodies is obtained from the hybrid hybridoma on deposit with the American Type Culture Collection, with Accession No. HB10501.

* * * * *